US009566012B2

(12) United States Patent
Greenhut et al.

(10) Patent No.: US 9,566,012 B2
(45) Date of Patent: Feb. 14, 2017

(54) METHOD AND APPARATUS FOR SELECTION AND USE OF VIRTUAL SENSING VECTORS

(71) Applicant: Medtronic, Inc., Minneapolis, MN (US)

(72) Inventors: Saul E. Greenhut, Aurora, CO (US);
Xusheng Zhang, Shoreview, MN (US);
Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/524,090

(22) Filed: Oct. 27, 2014

(65) Prior Publication Data

US 2016/0113536 A1  Apr. 28, 2016

(51) Int. Cl.
| | |
|---|---|
| A61B 5/04 | (2006.01) |
| A61N 1/39 | (2006.01) |
| A61B 5/042 | (2006.01) |
| A61B 5/0456 | (2006.01) |
| A61B 5/0452 | (2006.01) |
| A61B 5/0472 | (2006.01) |
| A61B 5/00 | (2006.01) |
| A61B 5/0205 | (2006.01) |
| A61N 1/37 | (2006.01) |
| A61B 5/0245 | (2006.01) |

(52) U.S. Cl.
CPC ......... *A61B 5/04011* (2013.01); *A61B 5/0205* (2013.01); *A61B 5/04012* (2013.01); *A61B 5/0422* (2013.01); *A61B 5/0452* (2013.01); *A61B 5/0456* (2013.01); *A61B 5/0472* (2013.01); *A61B 5/04525* (2013.01); *A61B 5/4836* (2013.01); *A61B 5/7282* (2013.01); *A61N 1/3702* (2013.01); *A61N 1/3925* (2013.01); *A61N 1/3956* (2013.01); *A61N 1/3987* (2013.01); *A61B 5/0245* (2013.01); *A61B 5/7275* (2013.01); *A61N 1/3962* (2013.01)

(58) Field of Classification Search
USPC ................................................ 600/512, 518
See application file for complete search history.

(56) References Cited

U.S. PATENT DOCUMENTS

| | | |
|---|---|---|
| 5,331,966 A | 7/1994 | Bennett et al. |
| 5,354,316 A | 10/1994 | Keimel |
| 5,545,186 A | 8/1996 | Olson et al. |
| 5,593,431 A | 1/1997 | Sheldon |

(Continued)

OTHER PUBLICATIONS

Baron et al., "Real-Time Assessment of Acute Myocardial Ischaemia by an Intra-Thoracic 6-Lead ECG: Evaluation of a New Diagnostic Option in the Implantable Defibrillator", Eurospace (2006), 8, pp. 994-1001.

(Continued)

*Primary Examiner* — Nicole F Johnson

(57) ABSTRACT

A medical device is configured to receive at least two physical cardiac electrical signals from a patient's heart via electrodes defining at least two physical sensing vectors. The medical device determines a signal feature for each of a plurality of virtual sensing vectors extending at a plurality of angles relative to one of the at least two physical sensing vectors during a known cardiac rhythm, compares the determined signal features and establishes criteria for confirming a suspected condition in response to the comparing.

36 Claims, 9 Drawing Sheets

(56) References Cited

U.S. PATENT DOCUMENTS

| | | |
|---|---|---|
| 6,393,316 B1 | 5/2002 | Gillberg et al. |
| 6,505,067 B1 | 1/2003 | Lee et al. |
| 7,031,771 B2 | 4/2006 | Brown et al. |
| 7,392,085 B2 | 6/2008 | Warren et al. |
| 7,496,409 B2 | 2/2009 | Greenhut et al. |
| 7,509,170 B2 | 3/2009 | Zhang et al. |
| 7,623,909 B2 | 11/2009 | Sanghera et al. |
| 7,627,367 B2 | 12/2009 | Warren et al. |
| 7,774,049 B2 | 8/2010 | Ghanem et al. |
| 7,783,340 B2 | 8/2010 | Sanghera et al. |
| 7,831,304 B2 | 11/2010 | Cao et al. |
| 7,890,159 B2 | 2/2011 | Zhang et al. |
| 7,904,153 B2 | 3/2011 | Greenhut et al. |
| 7,953,489 B2 | 5/2011 | Warren et al. |
| 7,991,471 B2 | 8/2011 | Ghanem et al. |
| 8,160,684 B2 | 4/2012 | Ghanem et al. |
| 8,175,708 B1 | 5/2012 | Snell et al. |
| 8,200,341 B2 | 6/2012 | Sanghera et al. |
| 8,244,349 B2 | 8/2012 | Sanghera et al. |
| 8,301,233 B2 | 10/2012 | Zhang et al. |
| 8,306,618 B2 | 11/2012 | Ghanem et al. |
| 8,380,293 B2 | 2/2013 | Zhang et al. |
| 8,391,956 B2 | 3/2013 | Zellers et al. |
| 8,437,842 B2 | 5/2013 | Zhang et al. |
| 8,600,489 B2 | 12/2013 | Warren et al. |
| 8,744,555 B2 | 6/2014 | Allavatam et al. |
| 8,825,145 B1 | 9/2014 | Zhang |
| 2003/0083586 A1 | 5/2003 | Ferek-Petric |
| 2006/0149337 A1 | 7/2006 | John |
| 2007/0156190 A1 | 7/2007 | Cinbis |
| 2007/0276445 A1 | 11/2007 | Sanghera et al. |
| 2007/0276452 A1 | 11/2007 | Sanghera et al. |
| 2008/0275516 A1 | 11/2008 | Ghanem et al. |
| 2008/0275521 A1 | 11/2008 | Warren et al. |
| 2009/0275998 A1 | 11/2009 | Burnes et al. |
| 2010/0010380 A1 | 1/2010 | Panken et al. |
| 2011/0020826 A1 | 1/2011 | Kornblith et al. |
| 2011/0144510 A1* | 6/2011 | Ryu .................. A61B 5/042 600/509 |
| 2011/0184300 A1 | 7/2011 | Shvilkin et al. |
| 2012/0245651 A1 | 9/2012 | Sanghera et al. |
| 2013/0066222 A1* | 3/2013 | Rosenberg .......... A61B 5/0464 600/518 |
| 2014/0148718 A1 | 5/2014 | Stickney et al. |

OTHER PUBLICATIONS

Zhang, "Method and Apparatus for Verifying Discriminating of Tachycardia Events in a Medical Device Having Dual Sensing Vectors", U.S. Appl. No. 14/255,158, filed Apr. 17, 2014, 65 pages.
(PCT/US2015/055925) PCT Notification of Transmittal of the International Search Report and the Written Opinion of the International Searching Authority, Mailed Jan. 5, 2016, 12 pages.

* cited by examiner

METHOD AND APPARATUS FOR SELECTION AND USE OF VIRTUAL SENSING VECTORS

TECHNICAL FIELD

The disclosure relates generally to implantable medical devices and, in particular, to a method and apparatus for generating and using virtual sensing vectors for monitoring cardiac electrical signals in an implantable medical device.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, e.g., implanted in the heart through one or more veins. Other leads may be non-transvenous leads implanted outside the heart, e.g., implanted epicardially, pericardially, or subcutaneously. In either case, the electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal cardiac rhythms. Upon detection of an abnormal rhythm, the device may deliver an appropriate electrical stimulation signal or signals to restore or maintain a more normal rhythm. For example, an IMD may deliver pacing pulses to the heart upon detecting tachycardia or bradycardia, and deliver cardioversion or defibrillation shocks to the heart upon detecting tachycardia or fibrillation.

SUMMARY

In general, the disclosure is directed to techniques for detecting or confirming a cardiac rhythm that involve computing virtual cardiac electrical signal features corresponding to virtual sensing vectors at predefined angles to a physical sensing vector. An implantable cardioverter defibrillator (ICD) operating in accordance with the techniques of this disclosure computes virtual cardiac electrical signals and/or virtual cardiac electrical signal features using physical cardiac electrical signals sensed along at least two physical sensing vectors defined by electrodes coupled to the ICD.

In one example, the disclosure provides a method, comprising receiving at least two physical cardiac electrical signals from a patient's heart via a plurality of electrodes that define at least two physical sensing vectors; determining a plurality of virtual cardiac electrical signal features using the at least two physical cardiac electrical signals during a first, known cardiac rhythm, each of the plurality of virtual cardiac electrical signal features corresponding to one of a plurality of virtual sensing vectors extending at a respective one of a plurality of angles relative to one of the two physical sensing vectors; comparing the determined signal features; establishing criteria for confirming a suspected condition in response to the comparing; detecting a suspected condition during a second, unknown cardiac rhythm; and confirming the suspected condition in response to the established criteria being met during the second, unknown cardiac rhythm.

In another example, the disclosure provides a medical device system, comprising a sensing module configured to receive at least two physical cardiac electrical signals via a plurality of electrodes that define at least two physical sensing vectors and a control module coupled to the sensing module. The control module is configured to determine a plurality of virtual cardiac electrical signal features using the at least two physical cardiac electrical signals during a first, known cardiac rhythm, each of the plurality of virtual cardiac electrical signal features corresponding to one of a plurality of virtual sensing vectors extending at a respective one of a plurality of angles relative to one of the two physical sensing vectors, compare the determined signal features, establish criteria for confirming a suspected condition in response to the comparing; detect a suspected condition during a second, unknown cardiac rhythm; and confirm the suspected condition in response to the established criteria being met during the second, unknown cardiac rhythm.

In another example, the disclosure provides a non-transitory, computer-readable storage medium comprising a set of instructions which, when executed by a control module of a medical device, cause the medical device to receive at least two physical cardiac electrical signals from a patient's heart via a plurality of electrodes that define at least two physical sensing vectors, determine a plurality of virtual cardiac electrical signal features using the at least two physical cardiac electrical signals during a first, known cardiac rhythm, each of the plurality of virtual cardiac electrical signal features corresponding to one of a plurality of virtual sensing vectors extending at a respective one of a plurality of angles relative to one of the two physical sensing vectors, compare the determined signal features, establish criteria for confirming a suspected condition in response to the comparing, detect a suspected condition during a second, unknown cardiac rhythm; and confirm the suspected condition in response to the established criteria being met during the second, unknown cardiac rhythm.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for sensing cardiac events for distinguishing between shockable arrhythmias and non-shockable arrhythmias. Shockable arrhythmias refer to abnormal heart rhythms for which a shock therapy, e.g., one or more cardioversion or defibrillation shocks, is delivered to one or both of the ventricles. Shockable arrhythmias may include ventricular tachycardia (VT) and ventricular fibrillation (VF). Shockable arrhythmias generally pose an immediate danger to the patient and therapy is needed in order to ensure the safety of the patient. Non-shockable arrhythmias, on the other hand, refer to normal or abnormal heart rhythms that typically do not require a shock therapy to be delivered to either of the ventricles. Non-shockable cardiac rhythms may include supra-ventricular tachycardia (SVT), which includes sinus tachycardia, atrial tachycardia (AT), atrial fibrillation (AF), atrial flutter, atrioventricular nodal reentrant tachycardia (AVNRT), atrioventricular reciprocating tachycardia (AVRT), or the like. Non-shockable arrhythmias do not generally pose an immediate danger to the patient. As such, non-shockable arrhythmias may go untreated, i.e., no shock therapy is delivered to the heart. In other instances, non-shockable arrhythmias may be treated using an electrical stimulation therapy, but the electrical stimulation therapy may be a relatively lower voltage pacing therapy or is not delivered to the ventricles of the patient.

A shock therapy generally includes at least one a high-voltage shock pulse, which may, for example, be in the range of at least 10 Joules and up to 35 Joules for transvenous lead systems carrying intracardiac cardioversion/defibrillation electrodes and in the range of at least 65 Joules and up to 80 Joules for subcutaneous lead systems carrying subcutaneous cardioversion/defibrillation electrodes.

Cardiac electrical signals, such as a subcutaneous electrocardiogram (ECG) or an intracardiac electrogram (EGM) are received via implanted electrodes and analyzed by an ICD to detect a shockable heart rhythm. The cardiac electrical signal includes cardiac event signals attendant to the depolarization (e.g., R-waves) and the repolarization (e.g., T-waves) of the ventricles. An ICD according to the present disclosure includes a tachyarrhythmia detection module configured to discriminate between shockable and non-shockable heart rhythms using virtual vector cardiac electrical signals.

Figure 1:
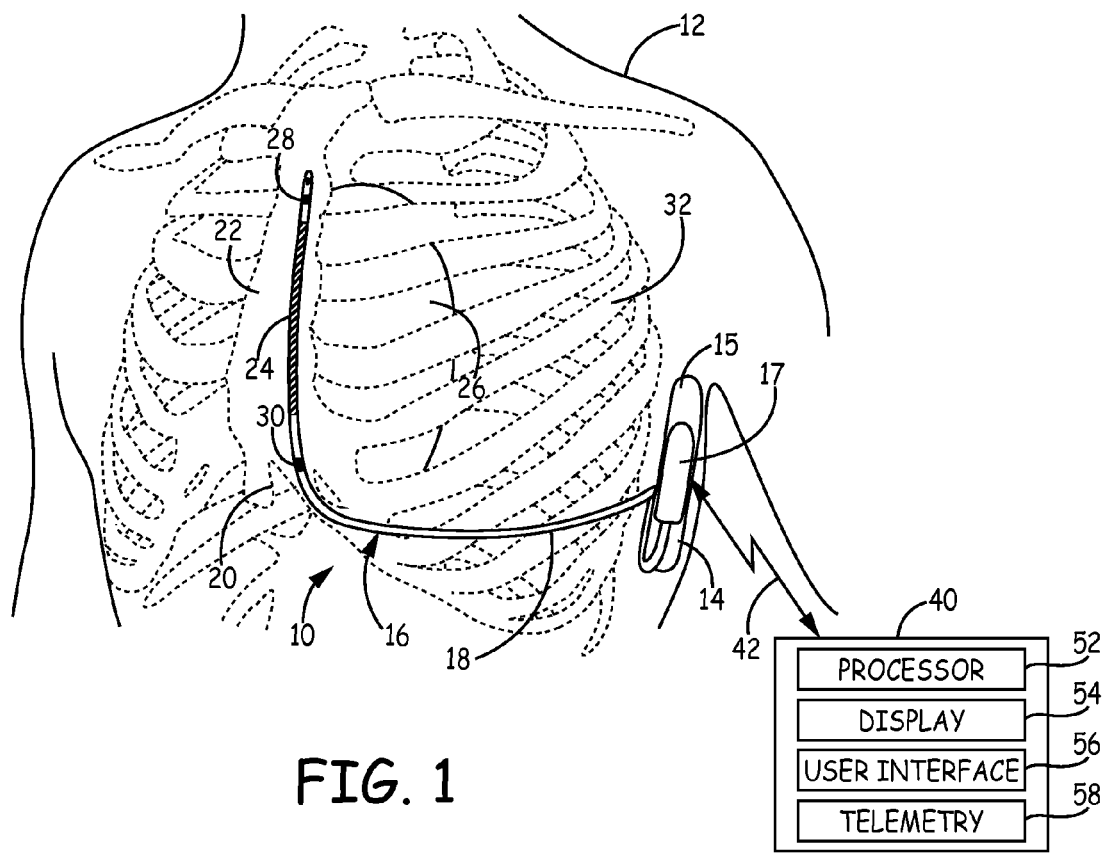
FIG. 1 is a conceptual diagram of a patient implanted with an example IMD system that includes an ICD coupled to a subcutaneous defibrillation and sensing lead.

FIG. 1 is a conceptual diagram of a patient 12 implanted with an example IMD system 10 that includes an ICD 14 coupled to a defibrillation lead 16. Defibrillation lead 16 includes a proximal end that is connected to ICD 14 and a distal end that includes one or more electrodes. Defibrillation lead 16 is illustrated in FIG. 1 as being implanted subcutaneously, e.g., in tissue and/or muscle between the skin and the ribcage 32 and/or sternum 22. Defibrillation lead 16 extends subcutaneously from ICD 14 toward xiphoid process 20. At a location near xiphoid process 20 defibrillation lead 16 bends or turns and extends subcutaneously superior, substantially parallel to sternum 22. Although illustrated as being offset laterally from and extending substantially parallel to sternum 22 in the example of FIG. 1, defibrillation lead 16 may be implanted over sternum 22, parasternally to the left of the sternum 22, parasternally to the right of the sternum 22 and may be angled laterally away from sternum 22 at either the proximal or distal end of lead 16.

Figure 2:
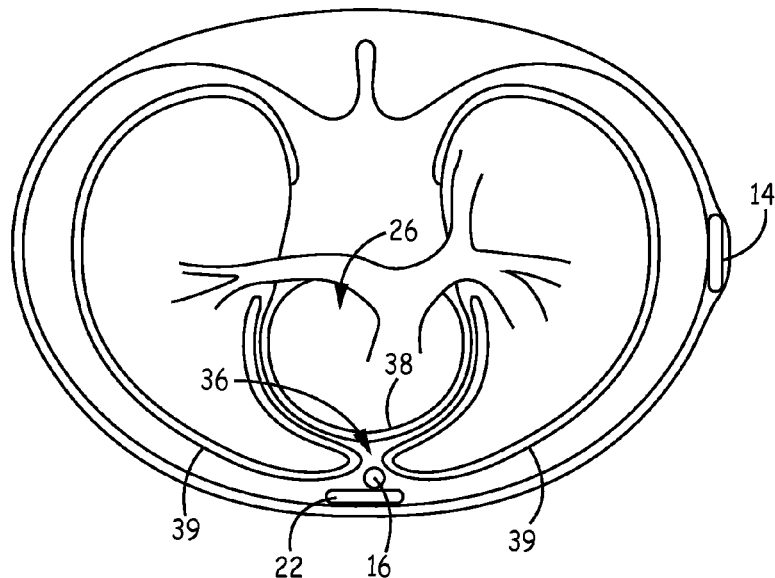
FIG. 2 is a transverse view of the patient in FIG. 1 depicting the defibrillation and sensing lead implanted in an alternate location.

In other instances, lead 16 may be implanted at other extravascular locations. As shown in a transverse view of patient 12 in FIG. 2, lead 16 may be implanted at least partially in a substernal location, e.g., between the ribcage 32 and/or sternum 22 and heart 26. In one such configuration, a proximal portion of lead 16 extends subcutaneously from ICD 14 toward sternum 22 (not seen in the transverse view of FIG. 2) and a distal portion of lead 16 extends superior under or below the sternum 22 in the anterior mediastinum 36. Anterior mediastinum 36 is bounded laterally by pleurae 39, posteriorly by pericardium 38, and anteriorly by sternum 22.

In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 26 and not above sternum 22 or ribcage.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posteriorly to the patient's back to a location opposite heart 26 such that the heart 26 is generally disposed between the ICD 14 and distal electrode coil 24 and distal sensing electrode 28.

Referring again to FIG. 1, lead 16 includes an elongated lead body 18 carrying electrodes 24, 28 and 30 located along the distal portion of the length of the lead body 18. Lead body 18 insulates one or more elongated electrical conductors (not illustrated) that extend from a respective electrode 24, 28 and 30 through the lead body 18 to a proximal connector (not shown) that is coupled to ICD 14. Lead body 18 may be formed from a non-conductive material, such as silicone, polyurethane, fluoropolymers, or mixtures thereof or other appropriate materials, and is shaped to form one or more lumens within which the one or more conductors extend. The conductors are electrically coupled to ICD circuitry, such as a therapy module or a sensing module, via connections in an ICD connector assembly 17 that includes a connector bore for receiving the proximal connector of lead 16 and associated electrical feedthroughs crossing ICD housing 15. The electrical conductors transmit therapy from a therapy module within ICD 14 to one or more of electrodes 24, 28, and 30, and transmit cardiac electrical signals from one or more of electrodes 24, 28, and 30 to the sensing module within ICD 14.

Defibrillation lead 16 is shown in FIG. 1 to include a defibrillation electrode 24, which may be an elongated coil electrode, along the distal portion of defibrillation lead 16. Defibrillation electrode 24 is located on lead 16 such that when ICD system 10 is implanted a therapy vector between defibrillation electrode 24 and a housing 15 of ICD 14 is substantially through or across the ventricle(s) of heart 26. In one example, all or a portion of housing 15 of ICD 14 may be formed of a conductive material, such as titanium or titanium alloy which may function as an electrode, sometimes referred to as a "CAN electrode."

Defibrillation lead 16 also includes one or more sensing electrodes 28 and 30, located toward the distal portion of defibrillation lead 16. In the example illustrated in FIG. 1, sensing electrodes 28 and 30 are separated from one another by defibrillation electrode 24. In other words, sensing electrode 28 is located distal to defibrillation electrode 24 and sensing electrode 30 is proximal to defibrillation electrode 24. ICD system 10 may sense electrical activity of heart 26 via one or more sensing vectors that include combinations of electrodes 28 and 30 and the housing 15. For example, ICD 14 may receive a subcutaneous ECG signal across a sensing vector between electrodes 28 and 30, a sensing vector between electrode 28 and the conductive housing 15, a sensing vector between electrode 30 and the housing 15, or any combination of electrodes 28, 30 and the housing 15. In some instances, ICD 14 may even sense cardiac electrical signals using a sensing vector that includes defibrillation electrode 24.

The various sensing vectors defined by electrodes 24, 28, 30 and housing 15 are referred to herein as "physical sensing vectors" because they are defined by electrodes at physical locations relative to heart 26. The actual locations of physical sensing vectors available in IMD system 10 will depend on the implant location of lead 16 and ICD 14 relative to each other and the locations of the electrodes 24, 28 and 30 along lead 16. Numerous configurations for physical sensing vectors are possible depending on the particular lead and electrode system used and the implant locations.

Figure 4:
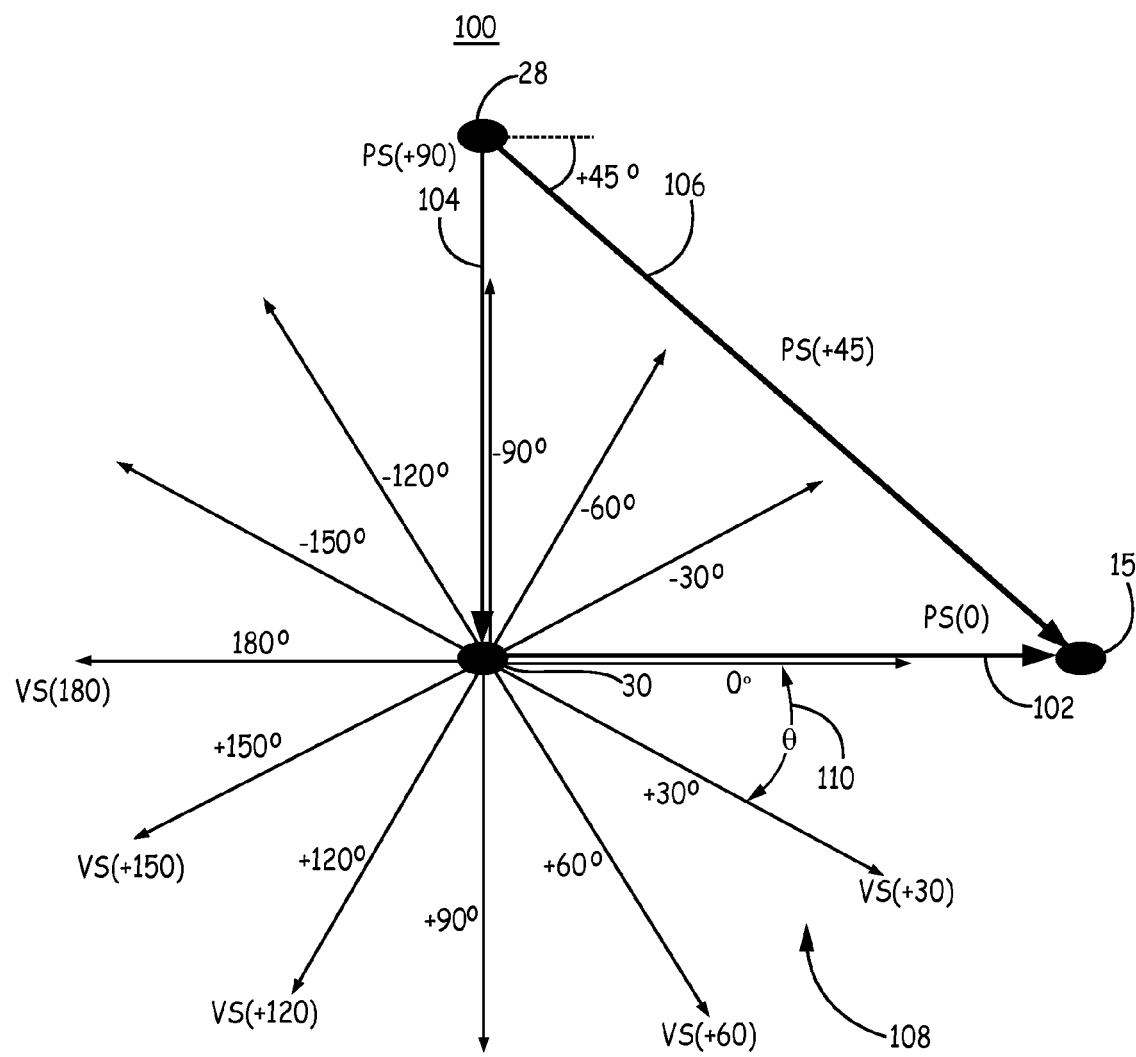
FIG. 4 is a conceptual diagram of physical sensing vectors of the IMD system of FIG. 1 and virtual sensing vectors at varying predefined angles θ from a physical sensing vector.

As described herein, e.g., in conjunction with FIG. 4, at least two physical sensing vector signals are used to compute multiple virtual cardiac electrical signals that are expected to occur along a virtual vector extending from the two physical sensing vectors at predetermined angles from the two physical sensing vectors. The virtual cardiac electrical signals are referred to herein as "virtual vector signals" because an electrode is not physically located along the vector corresponding to the computed virtual signal. The angle of the virtual vector signal, however, is predefined and used along with the physical sensing vectors to compute the virtual vector signal.

ICD 14 analyzes the physical cardiac electrical signals and the virtual cardiac electrical signals as described below to detect and treat shockable tachyarrhythmias, such as VT or VF. ICD 14 may deliver one or more cardioversion or defibrillation shocks via defibrillation electrode 24 in response to detecting VT or VF. ICD 14 may also provide pacing therapy, such as anti-tachycardia pacing (ATP) and/or post-shock pacing for treating bradycardia or asystole after a cardioversion or defibrillation shock when pacing capabilities are available.

Housing 15 forms a hermetic seal that protects internal electronic components of ICD 14. Housing 15 may function as a "CAN electrode" since the conductive housing or a portion thereof may be coupled to internal circuitry to be used as a sensing electrode or as an indifferent or ground electrode during cardioversion/defibrillation shock delivery. ICD 14 also includes connector assembly 17 (also referred to as a connector block or header) that includes electrical feedthroughs through which electrical connections are made between electrical conductors within lead 16 and electronic components included within the housing 15. As will be described in further detail herein, housing 15 may enclose one or more processors, memory devices, transmitters, receivers, sensors, sensing circuitry, therapy circuitry and other appropriate components.

The example illustrated in FIG. 1 is illustrative in nature and should not be considered limiting of the techniques described in this disclosure. In other examples, ICD 14 and one or more associated leads may be implanted at other locations for defining different physical sensing vectors. For example, ICD 14 may be implanted in a subcutaneous pocket in the right chest. In this case, defibrillation lead 16 may extend subcutaneously from the device toward the manubrium of the sternum 22 and bend or turn and extend subcutaneously or substernally inferiorly from the manubrium of the sternum, substantially parallel with the sternum.

The techniques disclosed herein may be implemented in numerous ICD and electrode configurations that include one or more housing-based electrodes and/or one or more lead-based electrodes for enabling sensing of physical cardiac electrical signals developed across one or more physical sensing vectors and for delivering electrical stimulation therapies to heart 26 including at least a shock therapy. The stimulation therapy is controlled based at least in part on virtual vector signals computed from the physical vector signals in some examples. The IMD system 10 is an extravascular IMD system because lead 16 is positioned in an extravascular location outside the blood vessels, heart 26 and pericardium 38. It is understood that while ICD 14 and lead 16 may be positioned between the skin and a muscle layer of the patient 12, ICD 14 and any associated leads could be positioned in any extravascular location of the patient, such as below a muscle layer or even within the thoracic cavity.

An external device 40 is shown in telemetric communication with ICD 14 by a communication link 42. External device may include a processor 52, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters and ECG signals retrieved from ICD 14. User interface 56 which may include a mouse, touch screen, key pad or the like to enable a user to interact with external device 40 to initiate a telemetry session with ICD 14 for retrieving data from and/or transmitting data to ICD 14. Telemetry unit 58 is configured for bidirectional communication with a telemetry module included in ICD 14 and is configured to operate in conjunction with processor 52 for sending and receiving data relating to ICD functions via communication link 42.

Communication link 42 may be established between ICD 14 and external device 40 using a radio frequency (RF) link such as Bluetooth, Wi-Fi, or Medical Implant Communication Service (MICS) or other RF bandwidth. External device 40 may be embodied as a programmer used in a hospital, clinic or physician's office to retrieve data from ICD 14 and to program operating parameters and algorithms in ICD 14 for controlling ICD 14 functions. External device 40 may be used to program ICD tachyarrhythmia detection parameters and criteria relating to the rate, intervals, and/or morphology of ECG cardiac event signals. External device 40 may also be used to program therapy control parameters, such as the shock energy used to terminate VT or VF. External device 40 may alternatively be embodied as a home monitor or hand held device.

Figure 3:
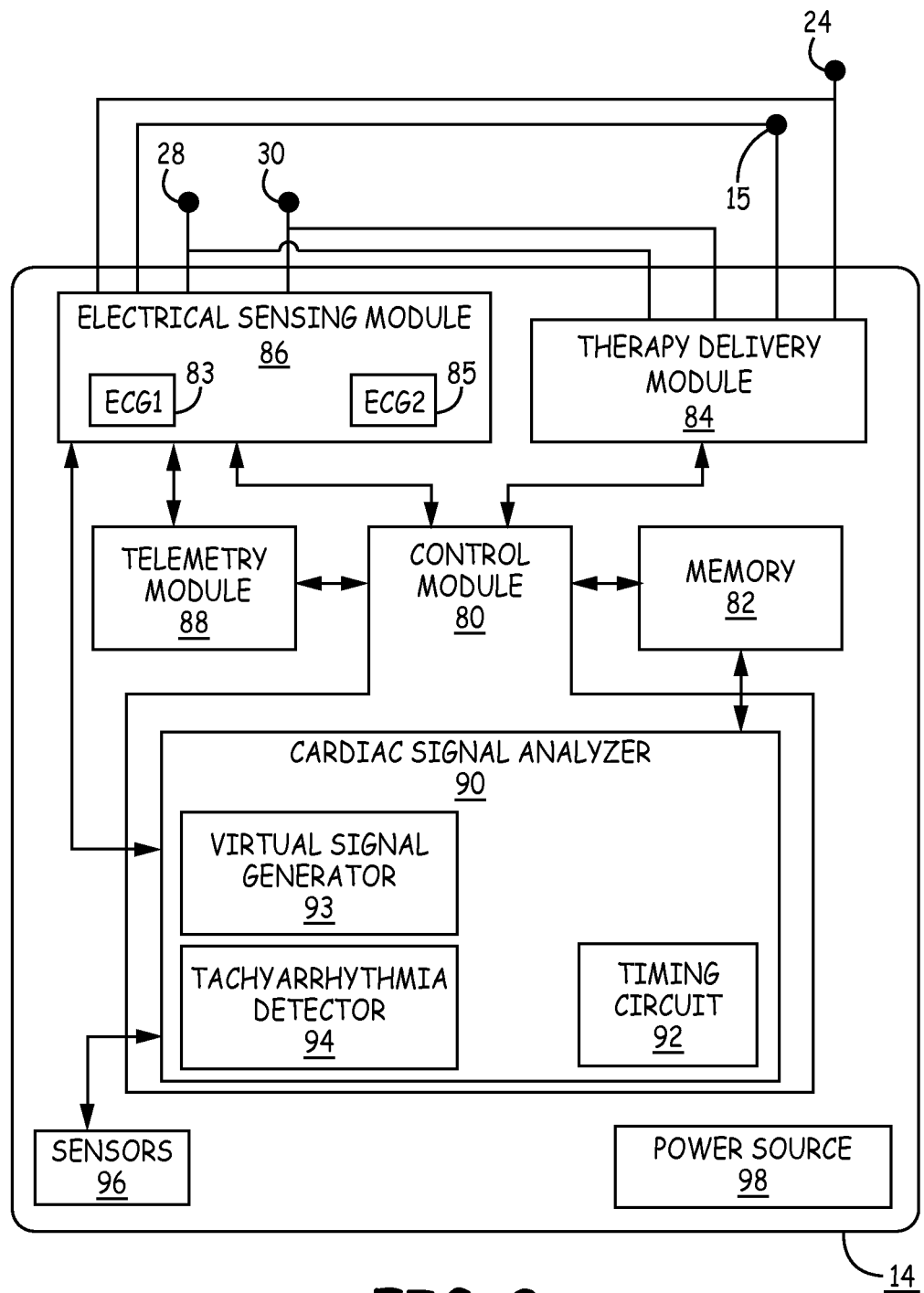
FIG. 3 is a schematic diagram of an ICD according to one embodiment.

FIG. 3 is a schematic diagram of ICD 14 according to one example. The electronic circuitry enclosed within housing 15 includes software, firmware and hardware that cooperatively monitor one or more physical and/or virtual ECG signals, determine when a cardioversion-defibrillation shock is necessary, and deliver prescribed cardioversion-defibrillation therapies. In some examples, ICD 14 may be coupled to a lead, such as lead 16, carrying electrodes, such as electrodes 24, 28 and 30, positioned in operative relation to the patient's heart for delivering cardiac pacing pulses in addition to shock therapies and may therefore include the capability to deliver low voltage pacing pulses as well as the high voltage shock pulses.

ICD 14 includes a control module 80 that includes a cardiac signal analyzer 90, memory 82, therapy delivery module 84, electrical sensing module 86, telemetry module 88. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, shockable rhythm detection operations performed by cardiac signal analyzer 90 for determining a need for therapy delivered by ICD 14 may be implemented in control module 80 executing instructions stored in memory 82.

As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD. Providing software, hardware, and/or firmware to accomplish the described functionality in the context of any modern IMD system, given the disclosure herein, is within the abilities of one of skill in the art.

Control module 80 includes cardiac signal analyzer 90 and communicates with therapy delivery module 84 and electrical sensing module 86 for sensing cardiac electrical activity, detecting cardiac rhythms, and controlling delivery of cardiac therapies in response to sensed physical and/or generated virtual vector signals. Therapy delivery module 84 and electrical sensing module 86 are electrically coupled to electrodes 24, 28, and 30 carried by lead 16 (shown in FIG. 1) and the housing 15, which may function as a sensing electrode or serve as a common or ground electrode during therapy delivery.

Electrical sensing module 86 is selectively coupled to electrodes 28, 30 and housing 15 in order to monitor electrical activity of the patient's heart. Electrical sensing module 86 may additionally be selectively coupled to electrode 24. Sensing module 86 is enabled to selectively monitor one or more physical sensing vectors selected from the available electrodes 24, 28, 30 and 15. For example, sensing module 86 may include switching circuitry for selecting which of electrodes 24, 28, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels 83 and 85 for sensing multiple physical ECG sensing vectors selected from electrodes 24, 28, 30 and housing 15. Sensing module 86 is shown to include two sensing channels 83 and 85 in the example of FIG. 3. Each sensing channel 83 and 85 may be configured to amplify, filter and rectify the ECG signal received from selected electrodes coupled to the respective sensing channel to improve the signal quality for sensing cardiac events, e.g., R-waves.

In one example, a first sensing channel 83 (ECG1) may be selectably configured to sense an ECG signal between sensing electrode 30 and ICD housing 15 which define a horizontal physical sensing vector. The second sensing channel 85 (ECG2) may be selectably configured to sense an ECG signal using electrodes 28 and 30 which define a vertical physical sensing vector. The sensing module 84 may alternatively be selectively configured to sense a physical cardiac electrical signal between sensing electrode 28 and ICD housing 15 defining a diagonal physical sensing vector. In other examples, one sensing channel 83 or 85 may receive an ECG signal using defibrillation electrode 24.

Each sensing channel 83 and 85 includes cardiac event detection circuitry for sensing cardiac events from the received ECG signal developed across the selected electrodes 24, 28, 30 or 15. Cardiac event sensing thresholds used by each sensing channel 83 and 85 may be automatically adjusted according to sensing control parameters, which may be stored in memory 82. Each sensing channel 83 and 85 senses a cardiac event when the respective received ECG signal crosses a respective auto-adjusting cardiac event sensing threshold.

Each time the received ECG signal crosses the sensing threshold for a given channel 83 or 85 outside a blanking interval, a cardiac event sense signal, also referred to herein as a "sense event signal" such as an "R-wave sense event signal," is produced and passed to control module 80 and/or cardiac signal analyzer 90. For example, R-wave sense event signals may be passed to tachyarrhythmia detector 94 and timing circuit 92 of cardiac signal analyzer 90 when a received ECG signal crosses the R-wave sensing threshold for a given channel 83 or 85. Sense event signals produced by sensing channel 83 or 85 may be used in detecting a shockable rhythm based on event intervals meeting VT or VF detection criteria.

Sensing module 86 may include an analog-to-digital converter for providing a digitized physical vector signal from one or both sensing channels 83 and 85 to control module 80 and/or cardiac signal analyzer 90. For example two physical vector signals as described above may each be converted to a multi-bit digital signal by sensing module 86 and provided to cardiac signal analyzer 90.

Cardiac signal analyzer 90 includes a virtual signal generator 93 configured to compute multiple virtual vector signals from at least two physical vector signals as described below in conjunction with FIG. 4. Cardiac signal analyzer 90 may use one or more virtual vector signals alone or in combination with physical vector signals received from sensing module 86 for monitoring the patient's heart rhythm, detecting a suspected condition such as T-wave oversensing or a shockable rhythm, and/or confirming a suspected condition. In some examples, virtual signal generator 93 senses cardiac events such as P-waves and R-waves from one or more virtual vector signals. Cardiac events are sensed when a virtual vector signal crosses a cardiac event sensing threshold. Cardiac event sense signals may therefore be produced by sensing module 86 in response to sensing threshold crossings by physical sensing vectors and by virtual signal generator 93 in response to sensing cardiac events from a virtual vector signal.

Cardiac signal analyzer 90 includes a tachyarrhythmia detector 94 for detecting and discriminating shockable and non-shockable rhythms. Tachyarrhythmia detector 94 may analyze one or more physical and/or virtual vector signals to determine if shockable rhythm detection criteria are met. Cardiac event sense signals, such as P-wave sense event signals and R-wave sense event signals, may be received from sensing module 86 and/or virtual signal generator 93 and used by tachyarrhythmia detector 94 for detecting a shockable rhythm and for determining a need for therapy.

Tachyarrhythmia detector 94 is configured to analyze physical vector signals received from sensing module 86 and virtual vector signals received from virtual signal generator 93 to select one or more physical sensing vector signals and/or virtual sensing vector signals for use as a monitoring signal for detecting a suspected shockable rhythm. Tachyarrhythmia detector 94 may be further configured to establish shockable rhythm detection criteria in response to determining and comparing signal features from the physical and virtual vector signals. Tachyarrhythmia detector 94 may analyze one or more detection signals selected from the available physical vector signals from sensing module 86 and computed virtual vector signals received from virtual signal generator 93 for confirming a suspected condition that is detected from a monitoring signal. If a detection signal meets the established shockable rhythm detection criteria, tachyarrhythmia detector 94 detects a shockable rhythm.

Cardiac signal analyzer 90 may further include a timing circuit 92 that includes various timers and/or counters for measuring time intervals, such as RR intervals or other sensed cardiac event intervals used by tachyarrhythmia detector 94 for detecting a shockable rhythm. The timing of R-wave sense event signals received from sensing module 86 and/or virtual signal generator 93 is used by timing circuit 94 to determine RR intervals between sense event signals. Tachyarrhythmia detector 94 may count RR intervals measured by timing circuit 92 that fall into different rate detection zones for determining a ventricular rate or performing other rate- or interval-based assessment for detecting ventricular tachyarrhythmia and discriminating shockable and non-shockable rhythms. Timing circuit 92 may control therapy delivery module to deliver a cardioversion/defibrillation shock in response to tachyarrhythmia detector 94 detecting a shockable rhythm. Timing circuit 92 may be configured to set various timers in response to sensed cardiac event signals, such as timers for controlling pacing escape intervals, signal analysis time segments or windows such as morphology template windows, morphology analysis windows relative to R-wave sense event signals, cardiac signal analysis time segments, T-wave windows, or other time intervals used by cardiac signal analyzer 90 for monitoring the patient's heart rhythm. Timing circuit 92 may be configured to perform other timing related functions for controlling therapy delivery including synchronizing cardioversion shocks or other therapies delivered by therapy delivery module 84 with sensed cardiac events.

Examples of algorithms that may be performed by ICD 14 for detecting, discriminating and treating shockable rhythms, which may be adapted to include techniques described herein using virtual vector signals for detecting shockable rhythms, are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening, shockable VT and VF.

Therapy delivery module 84 includes a high voltage (HV) therapy delivery module including one or more HV output capacitors and, in some instances, a low voltage therapy delivery module. When a shockable rhythm is detected the HV capacitors are charged to a pre-programmed voltage level by a HV charging circuit.

Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing 15. Timing circuit 92 may be used to control R-wave synchronized shock pulses delivered by therapy delivery module 84.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy. In some examples, sensors 96 include a posture sensor for producing a patient body posture signal received by control module 80. As described below, cardiac signal analyzer 90 may respond to a change in the patient body posture signal by selecting a different monitoring signal, a different detection signal, or different shockable rhythm detection criteria based on how a change in patient body posture influences the physical and/or virtual vector signals used by tachyarrhythmia detector 94 for detecting a shockable rhythm.

Certain steps in producing multiple virtual vector signals and analyzing physical and virtual vector signals may be performed by the cardiac signal analyzer 90 of control module 80 using instructions and control parameters stored in memory 82. User-programmable control parameters may be programmed into memory 82 via telemetry module 88. Telemetry module 88 includes a transceiver and antenna for communicating with external device 40 (shown in FIG. 1) using RF communication. Under the control of control module 80, telemetry module 88 may receive downlink telemetry from and send uplink telemetry to external device 40.

Physical and virtual vector signal data related to the detection of a shockable rhythm and the delivery of a cardioversion or defibrillation shock may be stored in memory 82 and transmitted by telemetry module 88 to external device 40 upon receipt of an interrogation command. Clinician review of episode data facilitates diagnosis and prognosis of the patient's cardiac state and therapy management decisions, including selecting programmable control parameters used for detecting shockable rhythms and delivering therapy.

In some examples, physical vector signals and or virtual vector signals may be transmitted to external device 40 from ICD 14. External processor 52 may perform some of the processes disclosed herein for computing virtual vector signals from the physical vector signals, analyzing the virtual vector signals for selecting one or more monitoring signals, selecting one or more detection signals, and establishing detection criteria based on a comparative analysis of the physical and virtual vector signals. Results of the analysis may be used by the external device to automatically program ICD 14 or recommend programmable parameters to a user via display 54 relating to vector signals and criteria used for detecting a shockable rhythm.

FIG. 4 is a conceptual diagram of physical sensing vectors 102, 104 and 106 and virtual sensing vectors 108 at varying angles θ from physical sensing vector 102. The physical sensing vectors 102, 104 and 106 are defined by the physical locations and polarities of sensing electrodes 28, 30 and housing 15. Sensing electrodes 28 and 30 and ICD housing 15 are shown schematically and are used to sense the physical cardiac electrical signals along the three different physical vectors 102, 104 and 106. Physical vector 102 between sensing electrode 30 and housing 15 is along a lateral axis of a substantially frontal plane of the patient and is referred to as a "horizontal" vector corresponding to a substantially horizontal orientation when the patient is in an upright position. Physical vector 104 between sensing electrodes 28 and 30 is along a cranial-caudal axis of the substantially frontal plane of the patient and is referred to as a "vertical" vector corresponding to a substantially vertical orientation when the patient is in an upright position. Physical vector 106 between electrode 28 and housing 15 is along a diagonal axis and is referred to herein as a "diagonal" vector. The locations and relative orientations of the physical vectors 102, 104 and 106 may vary between patients and IMD systems and are not limited to the particular horizontal, vertical, and diagonal axes shown or to a particular anatomical plane of the patient. In some examples, four or more electrodes may be implanted and coupled to ICD 14 for using four or more physical sensing vectors for computing virtual vector signals. While a two dimensional virtual vector system is shown in FIG. 4, it is contemplated that a three-dimensional virtual vector system could be utilized in which virtual vectors are computed in more than one plane using four or more electrodes that define at least four physical vector signals.

The illustrative example of the locations and orientations of the physical vectors 102, 104 and 106 shown in FIG. 4 is convenient to illustrate the concept of computing multiple virtual sensing vectors at varying angles from one of the physical vectors. Using the convention of the left pointing horizontal physical vector 102 being the 0 degree vector, positive vectors being defined in a clockwise direction from the 0 degree vector, and negative vectors being defined in a counter-clockwise direction from the 0 degree vector, a cardiac signal sensed along horizontal physical vector 102 is referred to as the PS(0) physical vector signal. A cardiac signal sensed along the vertical vector 104 is referred to as the PS(+90) physical vector signal. In the example shown, electrode 30 has a positive polarity so that the direction of the physical vector 104 is in the direction of the +90 vector angle (clockwise) with respect to horizontal vector 102 in the convention shown. The opposing virtual vector directed toward −90 degrees (counterclockwise) with respect to the horizontal physical vector 102 is associated with a virtual signal VS(−90), equal but opposite in polarity from the physical vector signal PS(+90). Likewise, the virtual vector directed toward 180 degrees, opposite the horizontal physical vector 102 would have a virtual vector signal VS(180) equal but opposite in polarity from the horizontal physical vector signal PS(0).

Using the two physical vector signals 102 and 104, the virtual signal VS(θ) along multiple virtual vectors 108 extending at varying angles θ from the horizontal vector 102 may be mathematically computed along multiple virtual vectors. In the example shown, the physical vectors 102 and 104 are substantially orthogonal, which may provide greater accuracy of computed virtual vector signals or virtual vector signal features, however, two physical vector signals used to compute virtual vector signals or virtual signal features are not required to be orthogonal. Different trigonometric relationships may be used to compute the virtual vector signals from two physical vector signals that are not orthogonal.

The third diagonal vector may provide a physical signal PS(+45) when the distances between electrode 28 and housing 15 and electrode 30 and housing 15 are equal. If these distances are unequal, the third diagonal vector may be a different vector angle. In either case, the diagonal physical vector signal received along diagonal vector 106 may be used in mathematical computations of virtual vector signals in some examples.

In one example, a virtual signal VS(+30) is computed by the virtual signal generator 93 as a cardiac electrical signal expected along a virtual vector 108 extending at angle θ=+30 degrees from the PS(0) physical vector 102 using trigonometric relations given by the equation:

$$VS(+30)=PS(0)*\cos(30°)+PS(+90)*\sin(30°)$$

The physical signals PS(0) and PS(+90) used in the above equation are received by the sensing module 86 via the electrodes 28, 30 and housing 15, which define the physical vectors 102 and 104. More generally, a virtual signal VS(θ) may be computed for a virtual vector at any angle θ from horizontal vector 102 along a substantially frontal plane of the patient by the equation:

$$VS(θ)=PS(0)*\cos(θ)+PS(+90)*\sin(θ).$$

The substantially orthogonal physical vector signals PS(0) and PS(+90) may be used to compute multiple virtual signals corresponding to predefined angles θ between 0 degrees and 180 degrees. For example, the above equation may be used to compute virtual signals VS(+30), VS(+60), VS(+120) and VS (+150). The opposite virtual signals, VS(−150), VS(−120), VS(−60), and VS(−30), respectively corresponding to negative angle virtual vector signals are equal to but opposite in polarity of the respective virtual signals at positive angles.

Any number of virtual signals may be computed from the physical cardiac signals received along any two of the physical vectors 102, 104 and 106 using trigonometric functions. In some examples, the number of virtual vector signals that are computed by the ICD 14 and their respective angles θ relative to one of the physical sensing vectors 102 are predefined. For example, four virtual vectors VS(+30), VS(+60), VS(+120) and VS (+150) may be computed. Other techniques for determining virtual vector signals are disclosed in U.S. Pat. No. 6,505,067 (Lee, et al.), incorporated herein by reference in its entirety. In the IMD system 10 of FIG. 1, any number of the three physical vector signals received along physical vectors 102, 104 and 106 and/or virtual vector signals computed from the physical vector signals may be used by ICD 14 for use in monitoring a patient's heart rhythm and detecting shockable rhythms.

In other examples, the polarities of electrodes 28, 30 and housing 15 (or an electrode along housing 15) may be reversed such that the physical vectors 102, 104 and 106 may have the opposite directions to those shown in FIG. 4. It is understood that the equations used to compute the virtual vector signals may be modified as needed, for example by a sign change or a trigonometric function change, to compute a virtual vector signal along a desired virtual vector 110 based on the direction of the physical vectors 102, 104 and 106 (defined by their physical locations and polarities) and the trigonometric relationship between the virtual vector 108 at a predetermined angle 110 from one of the physical vectors 120, 104, 106.

As used herein, the "cardiac electrical axis" refers to one of the physical vectors from which a physical vector signal is received by the ICD 14, or one of the virtual vectors for which a virtual vector signal may be computed by the ICD 14, that is identified as being the vector most closely aligned with the mean direction of the action potentials traveling through the ventricles during ventricular depolarization. The ventricular depolarization is represented by the QRS complex in the physical and virtual sensing vector signals and is used as a basis for determining the cardiac electrical axis from among the physical vector signals received by ICD 14 and the virtual vector signals that may be computed by ICD 14 at predefined angles from one of the physical sensing vectors.

Since cardiac depolarization begins in the right atrium and is conducted to the right and left ventricles, and the left ventricle typically has greater myocardial mass than the right ventricle, the cardiac electrical axis may typically be between 0 degrees and +90 degrees during sinus rhythm in a normal heart. If the depolarizations arise from one or more ectopic locations and/or travel in non-normal conduction patterns, e.g., along retrograde or re-entrant circuits, the cardiac electrical axis will change. Accordingly, a change in the cardiac electrical axis may be used by cardiac signal analyzer 90 to discriminate between heart rhythms in some examples.

As described below, different physical and virtual signals may differ from each other in signal-to-noise ratio, cardiac event amplitudes, e.g., different P-wave, R-wave and T-wave amplitudes, and other signal features. Furthermore, features of a physical or virtual signal along a given vector may change due to an abnormal heart rhythm. Inter-signal and intra-signal differences may be used for selecting optimal vector(s) for monitoring cardiac electrical signals, and inter- and intra-signal changes as well as changes in the cardiac electrical axis may be used by ICD 14 for detecting shockable rhythms.

Figure 5:
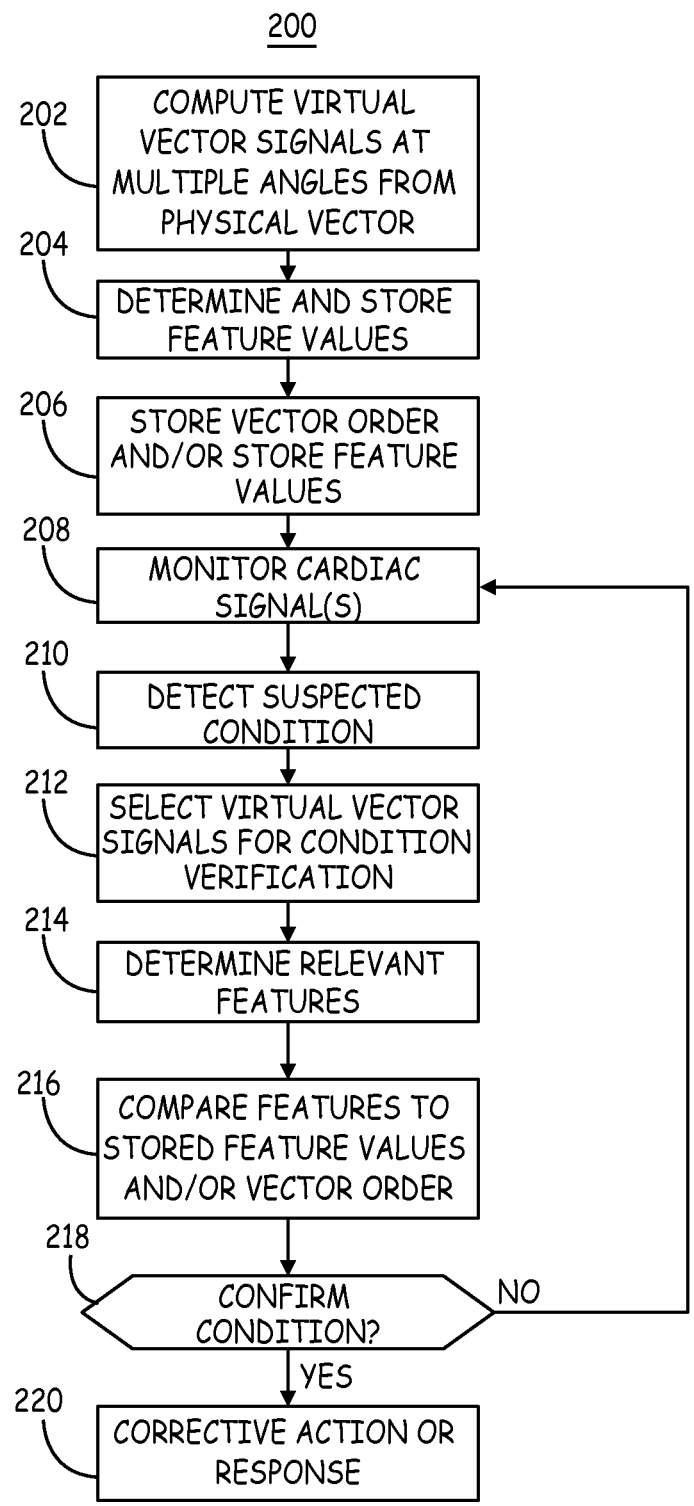
FIG. 5 is a flow chart of a method performed by the ICD of FIG. 1 according to one example.

FIG. 5 is a flow chart 200 of a method performed by ICD 14 using virtual vector signal features for detecting a condition according to one example. Flow chart 200 provides an overview of a method for using virtual vector signals for detecting a condition and controlling an ICD response to the detected condition. More specific examples of using virtual vectors by ICD 14 are described below in conjunction with FIGS. 6 through 9. Initially, at block 202, a desired number of virtual vector signals may be computed by virtual signal generator 93 using at least two physical vector signals received from sensing module 86, which may be selected from physical sensing vectors 102, 104 and 106. In the illustrative example given above, four virtual vector signals VS(+30), VS(+60), VS(+120) and VS (+150) are computed at the given predetermined vector angles of +30, +60, +120, and +150 degrees from physical sensing vector 102. In other examples, more or fewer virtual vector signals may be computed, e.g. at 10 degree vector angle increments, 15 degree vector angle increments, 20 degree vector angle increments, 30 degree vector angle increments, 45 degree vector angle increments or other angle increments or any combination thereof. The virtual vector angles relative to physical sensing vector 102 (or another physical sensing vector) are predetermined angles since the angle is used in the trigonometric relations used to compute the virtual vector signals.

Signal feature values are determined at block 204 for each of the at least two physical vector signals and the computed virtual vector signals. Signal features may be determined at block 204 during a known cardiac rhythm, e.g., during a known supraventricular rhythm or other non-shockable rhythm. The signal features may include signal features that are used in a detection algorithm for confirming a suspected condition. For example, signal features may be determined that are used for detecting a shockable rhythm or for assessing signal quality for verifying the reliability of signal sensing for detecting a shockable rhythm. Signal features may include, with no limitation intended, the amplitude, width, slope, waveform morphology, normalized waveform area, variation of signal morphology between cardiac cycles, variation of normalized waveform area between cardiac cycles, or other features of P-waves, R-waves, and/or T-waves. In one example, the amplitude, width or area of the R-wave and the amplitude, width or area of the T-wave are determined for each physical and virtual vector signal by cardiac signal analyzer 90. In some examples, virtual vector signal features may be determined at block 204 by computing only a segment of virtual vector signals at block 202.

The feature values determined for each vector may be stored in memory 82 at block 206. Additionally or alternatively, the physical and virtual vectors may be ordered according to the greatest to smallest (or smallest to greatest) value of a given feature. For example, if two physical vector signals and four virtual vector signals are being analyzed, the six physical and virtual sensing vectors may be ordered from greatest feature value, e.g., maximum rectified peak R-wave amplitude, to smallest feature value.

A distinct vector order may be stored for multiple signal features, e.g., one vector order may be stored for maximum peak R-wave amplitude, another vector order may be stored for maximum peak T-wave amplitude, and another vector order may be stored for QRS width. In some examples, the feature values are determined from rectified signals, but feature values may be determined from non-rectified signals in some examples. The actual signal feature values are not necessarily stored at block 206 with the ordered vector identities in some examples. Only the vector orders may be stored at block 206 for each of the signal features determined at block 204. A change in vector order may be used by cardiac signal analyzer 94 for detecting a shockable rhythm in some examples.

One or more of the physical and/or virtual vector signals are monitored at block 208 for detecting a shockable rhythm. In some examples, only physical signals are monitored on a continuous or substantially continuous basis. One or more virtual vector signals are computed and analyzed only when a suspected condition is detected to confirm the suspected condition. In this way, processing power for computing and analyzing virtual vectors may be conserved. In other examples, one or more virtual vector signals may be selected as monitoring signals at block 208, instead of or in addition to one or more physical vector signals to provide an optimal signal for detecting a suspected condition. In this case, the virtual vector signal may be computed and monitored continuously by cardiac signal analyzer 90 instead of only when a suspected condition is detected. When referring to monitoring a virtual vector signal (or using a virtual vector signal for confirming a suspected condition) in the methods disclosed herein, it is recognized that in some cases it is a computed virtual vector signal feature that is being monitored or used without requiring computation of the virtual vector signal on a continuous basis. In other cases, the virtual vector signal is computed continuously at the same sampling rate of the physical vector signals and may be compared to a cardiac event sensing threshold, for example, as it is computed for detecting cardiac events such as R-waves. Methods for selecting virtual vectors used for monitoring a virtual vector signal or virtual vector signal feature for detecting a suspected condition are described below in conjunction with FIG. 8.

At block 210, a preliminary detection of a suspected condition may be made based on the monitored signals. The suspected condition may be a shockable rhythm, T-wave oversensing, or other condition that may be confirmed by additional signal analysis. The suspected condition may be detected at block 210 using criteria that require relatively low processing power and signal analysis complexity. For example, a suspected condition may be detected by tachyarrhythmia detector 94 based on RR intervals determined between sensed R-wave event signals received from sensing module 86 or virtual signal generator 93.

At block 212, one or more virtual vector signals may be selected for analysis by cardiac signal analyzer 90 for confirming the suspected condition. One or more virtual vector signals may be selected at block 212 based on signal features that provide the greatest sensitivity and/or specificity for detecting the suspected condition out of the available virtual and physical vectors. For example, as described below, a virtual vector may be identified that provides the greatest discrimination between shockable and non-shockable rhythms based on one or more particular signal features.

One or more detection features are determined at block 214 from the vector(s) selected at block 212. Detection features are features that are used for confirming the suspected condition. For example, if the suspected condition is a shockable rhythm, at least one signal feature used to discriminate a shockable from a non-shockable rhythm is determined at block 214 for each of the vectors selected at block 212. The determined features are analyzed at block 216 to confirm the suspected condition. For example, signal features determined for one or more virtual vectors may be compared to detection criteria defined for confirming the particular condition, e.g., shockable rhythm detection criteria for confirming a shockable rhythm. In other examples, analogous signal features are determined for multiple virtual vectors at block 212. The virtual (and physical) vectors may be ordered according to the analogous feature values at block 216. The vector order is compared to the vector order stored at block 204 for the given feature. A change in the vector order is evidence confirming detection of the suspected condition.

If the suspected condition is confirmed at block 218, a corrective action or response is taken at block 220. For example, if a shockable rhythm is detected and confirmed, a therapy may be delivered at block 220. If oversensing is detected and confirmed, a therapy may be withheld at block 220.

Figure 6A:
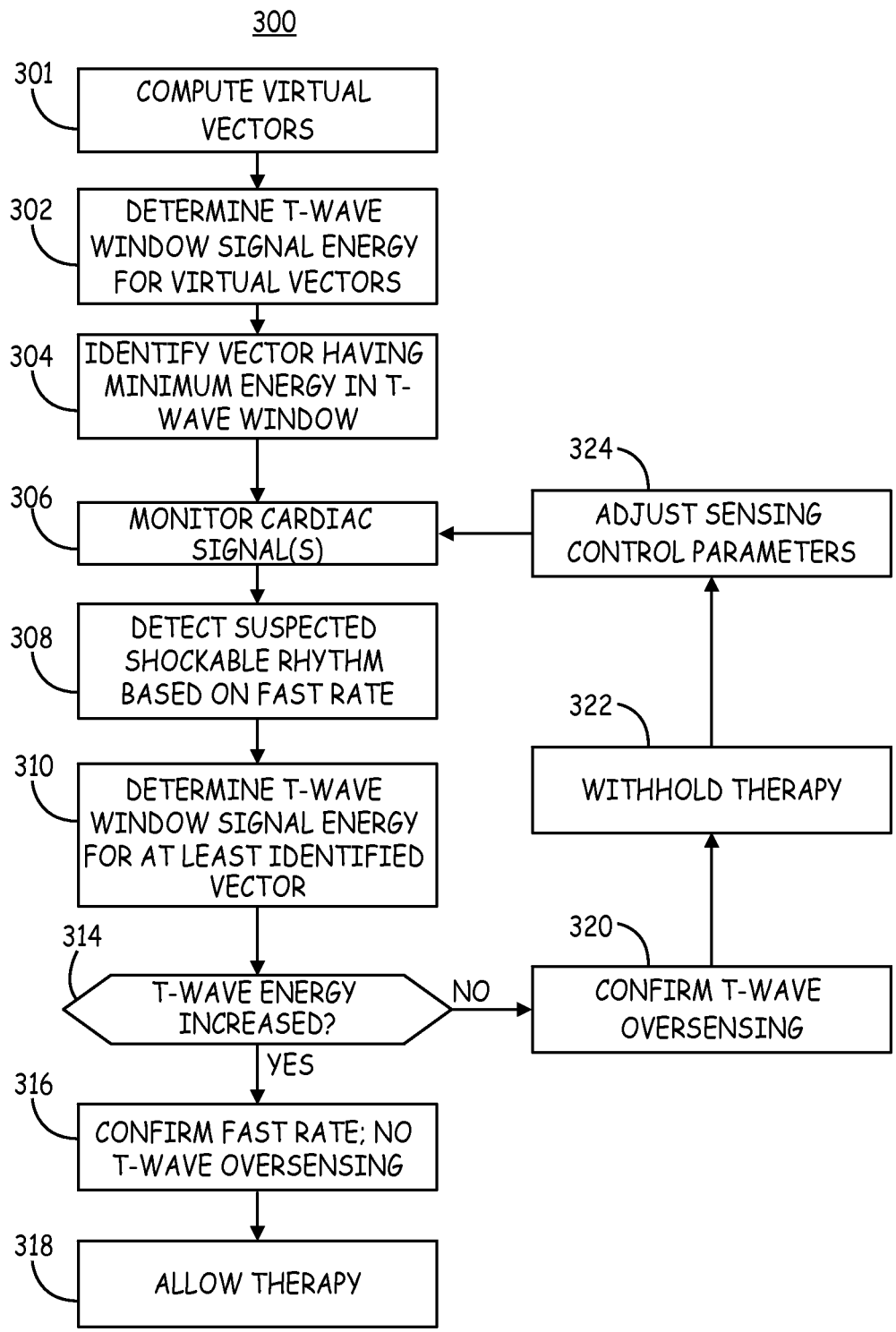
FIG. 6A is a flow chart of a method for detecting T-wave oversensing using virtual vector signals according to one example.

FIG. 6A is a flow chart 300 of a method for detecting T-wave oversensing using virtual vector signals according to one example. During a known, non-shockable rhythm, multiple virtual vector signals may be computed from at least two physical vector signals at block 301 as described above. At block 302, a T-wave window is set relative to sensed R-waves for each computed virtual vector signal, and optionally each physical vector signal. The signal energy during the T-wave window is determined for each virtual vector signal, and optionally each physical vector signal.

The term "T-wave window signal energy" as used herein generally refers to the strength or largeness of the T-wave signal during the T-wave window relative to the virtual signal baseline and may generally be determined based on the amplitude of one or more signal sample points during the T-wave window. The T-wave window signal energy may be determined as a maximum absolute peak amplitude during the T-wave window, summing the absolute value of the amplitude of all signal sample points in the T-wave window, or summing the squared amplitudes of all signal sample points in the T-wave window in various examples. In other examples, all signal peaks crossing an amplitude threshold within the T-wave window may be counted as a determination of T-wave signal energy.

The vector having a minimum T-wave window signal energy is identified at block 304. The vector having the minimum T-wave window signal energy may be determined out of only the virtual vectors or out of the virtual vectors and one or more of the physical vectors.

At block 306, one or more selected vector signals are monitored for detecting a suspected shockable rhythm. The physical vectors signals received by ECG sensing channels 83 and 85 may be monitored at block 306 in some examples. In other examples, one or more virtual vector signals (or virtual vector signal features) may be monitored in addition to or instead of physical vector signals. At block 308, a fast heart rate is detected based on the monitored signal(s) meeting a rate-based shockable rhythm criterion. For example, a fast heart rate may be detected when a required number of RR intervals that are shorter than a VT/VF detection interval are detected. To illustrate, if 12 out of the most recent 18 RR intervals are less than a predetermined VT interval threshold, e.g., less than 300 ms, a fast rate is detected at block 308. In other examples, other criteria, e.g., other rate based criteria, criteria relating to signal morphology or event patterns, or criteria relating to other sensor signals, may be used to detect a suspected shockable rhythm in addition to or alternatively to the example of the rate-based criteria described here.

When a fast rate is detected based on RR intervals, T-wave oversensing (TWOS) may be suspected. T-waves that are falsely sensed as R-waves may cause a rate-based shockable rhythm criterion to be met and lead to a false detection of a shockable rhythm and unnecessary therapy delivery. In order to avoid false shockable rhythm detection, the T-wave window signal energy may be re-determined at block 310 from the vector signal previously identified (block 304) to have the minimum T-wave window signal energy. In some examples, the T-wave window signal energy is re-determined for detecting the presence of TWOS any time a fast ventricular rate is detected. In other examples, the T-wave window signal energy is re-determined when other TWOS criteria are detected other than or in addition to the fast ventricular rate.

In some examples, the T-wave window signal energy is re-determined using the same technique used at block 304 for determining T-wave signal energy. For example, a T-wave window may be set following an R-wave sense event signal received from sensing module 86 based on either of ECG1 83 or ECG2 85 crossing an R-wave sensing threshold or following an R-wave sense event signal received from virtual signal generator 93. During the known cardiac rhythm, the R-wave sense event signals are highly likely to be true R-waves. The T-wave window set to begin after a true R-wave sense event signal during a known cardiac rhythm will provide a properly placed window relative to the true T-wave for determining the T-wave signal energy at block 304.

During a fast unknown rhythm or suspected TWOS, however, some R-sense event signals may be false sense event signals caused by sensing a T-wave in the physical or virtual vector signal. As such, the T-wave window set for determining T-wave signal energy relative to an R-wave sense event signal may be set differently at block 314 than at block 304. Since the sense event during the fast unknown rhythm could be a T-wave, the T-wave window may be set to include the sense event signal rather than to begin after the sense event signal. In this situation, some T-wave windows may include true R-waves and some may include true T-waves if TWOS is occurring. The signal energy during at least two consecutive T-wave windows is determined in some examples. In some examples, the T-wave signal energy for multiple consecutive signals may be determined and averaged, alternating T-wave window signal energies may be compared, alternative T-wave signal energies may be grouped and compared, or an average T-wave signal energy for alternating R-wave sense event signals may be determined.

In other examples, R-wave sense event signals produced by sensing module 86 based on the physical vector signal(s) 83 and 85 may be identified as being suspected TWOS events. Suspected TWOS events may be identified according to techniques generally disclosed in commonly assigned U.S. Pat. No. 7,831,304 (Cao, et al.), incorporated herein by reference in its entirety. T-wave windows may be defined for determining a T-wave window signal energy for the virtual vector identified at block 304 only for R-wave sense event signals that meet suspected TWOS event criteria.

At block 314, the re-determined T-wave window signal energy is compared to the minimum T-wave window signal energy determined previously at block 304 for the same vector. If the T-wave window signal energy has generally increased, as determined at block 314, the signal may be a valid R-wave during the T-wave window and is being properly sensed. The fast rate is verified at block 316 as being a valid fast ventricular rate that is not caused by TWOS. Therapy for treating the fast rate is allowed at block 318, pending a shockable rhythm detection based on additional shockable rhythm detection criteria.

The comparison made at block 314 to detect an increased T-wave window signal energy may include determining if the signal energy for both of at least two consecutive T-wave windows is higher than the minimum T-wave signal energy. If both of at least two consecutive T-wave windows have increased signal energy suggesting that an R-wave is present in the T-wave windows, both of the corresponding R-wave sense event signals used to set the T-wave windows are deemed valid. The fast rate is verified at block 316 and TWOS is not detected. A higher signal energy in both of the at least two T-wave windows is evidence of a higher amplitude R-wave in both windows being properly sensed as a true R-wave.

If at least one of the T-wave windows does not have a higher signal energy than the minimum T-wave signal energy determined at block 304, TWOS is detected at block 320. The corresponding R-wave sense event signal is deemed invalid and may be an oversensed T-wave or other signal noise on the physical vector signal. If the T-wave window signal energy is not increased at block 314 in the vector signal previously identified to have the minimum T-wave window signal energy, then the fast rate detected at block 308 may be due to TWOS. TWOS is verified at block 320 and a shockable rhythm therapy is withheld, at least temporarily, at block 322. In addition to withholding a shockable rhythm therapy in response to detecting TWOS, one or more sensing control parameters may be adjusted at block 324. For example, sensing module 86 may select a different physical vector signal for monitoring at block 306 and/or a sensing threshold may be adjusted to reduce the likelihood of TWOS.

Figure 6B:
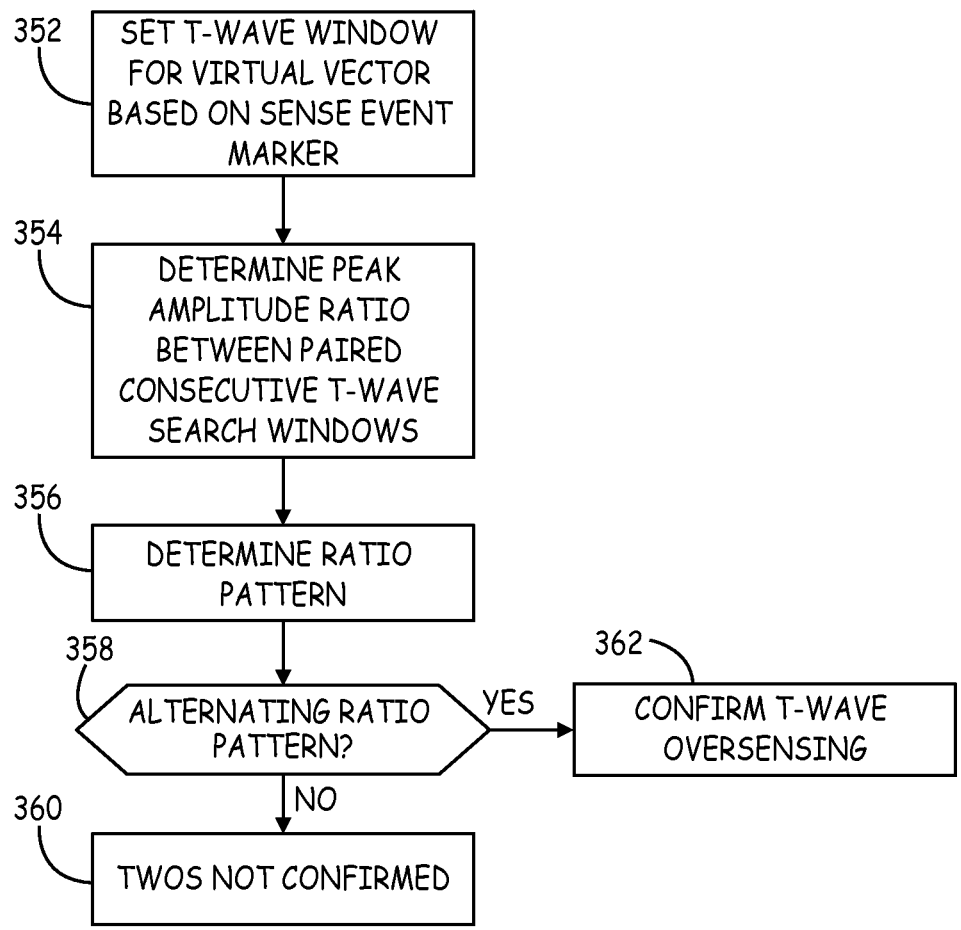
FIG. 6B is a flow chart of a method that may be performed at blocks 310 and 314 of FIG. 6A for determining if the T-wave window signal energy is increased in at least one virtual vector.

FIG. 6B is a flow chart 350 of a method that may be performed at blocks 310 and 314 of FIG. 6A for determining if the T-wave window signal energy is increased in at least one virtual vector. At block 352, R-wave sense event signals produced by sensing module 86 based on the physical vector signal(s), e.g., two of PS(0) 102, PS(+90) 104, or PS(+45) 106 received by sensing channels ECG1 83 or ECG2 85, are used to set T-wave windows for determining the virtual vector T-wave window energy in at least one virtual vector. The vector identified at block 304 (FIG. 6A) having the minimum T-wave window signal energy may be used at block 352.

At block 354, the maximum absolute peak amplitudes or other indication of signal energy during consecutive pairs of T-wave windows is determined. In one example, the maximum absolute peak amplitudes are determined for each T-wave window and ratios or differences between consecutive pairs of amplitudes are determined. At block 356 a pattern of the ratio or differences is determined. For example, if the ratio is less than 0.5 the ratio is classified as small. If the ratio is greater than 1.5, the ratio is classified as large. If the ratio is between 0.5 and 1.5, the ratio is classified as medium. If a pattern of consecutively determined ratios of peak absolute amplitudes of paired T-wave windows is large-small-large-small, then this alternating ratio pattern is detected at block 358 as evidence to confirm TWOS at block 362. If an alternating pattern of consecutive T-wave amplitude ratios or other indication of alternating T-wave window signal energy is determined for consecutive T-wave windows of the virtual vector is not detected, TWOS is not confirmed at block 360. In some examples, an alternating pattern of T-wave signal energy in at least one virtual vector is evidence of TWOS and the suspected TWOS is confirmed. A suspected shockable rhythm is not confirmed based on confirming TWOS in some examples.

Figure 7:
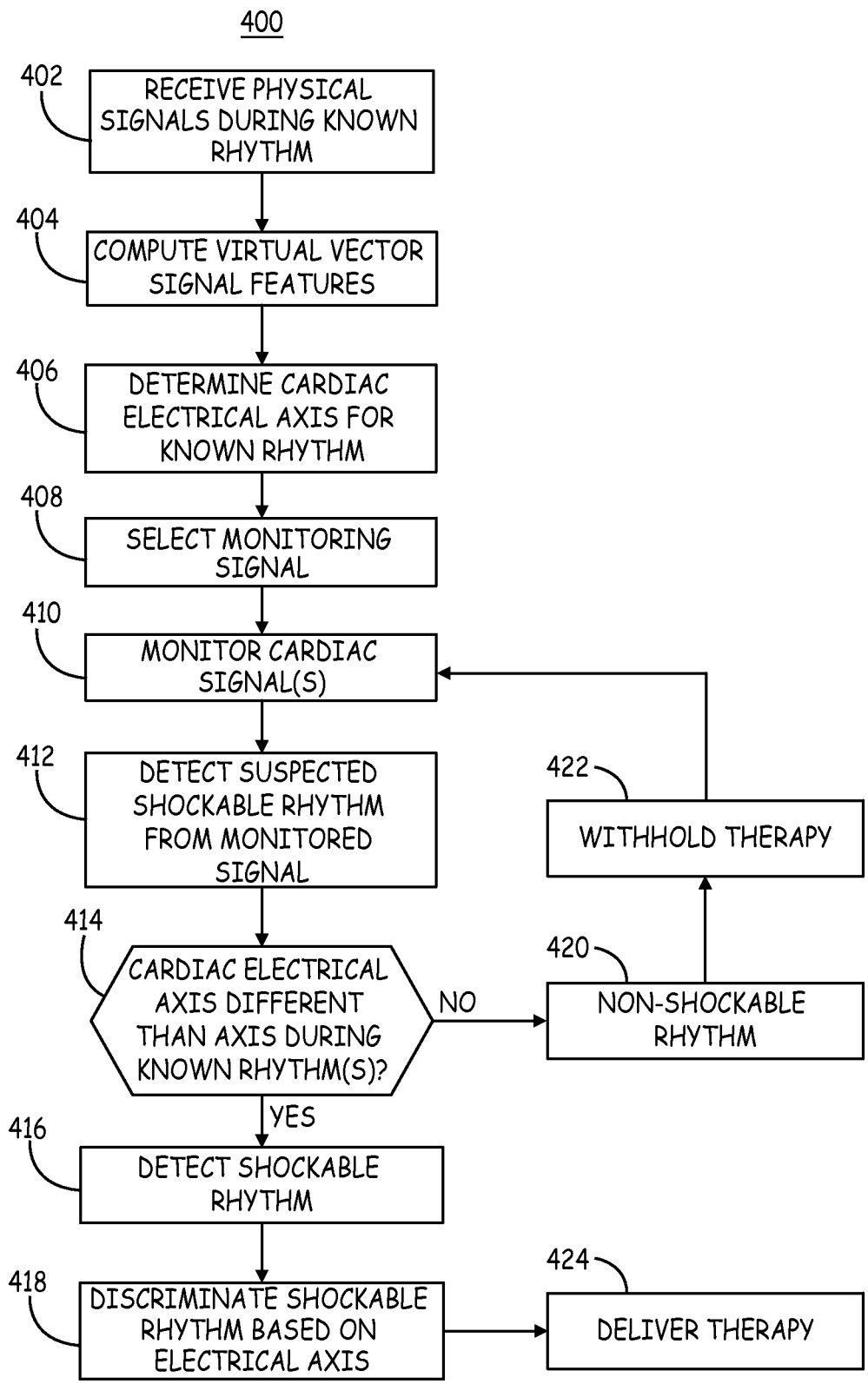
FIG. 7 is a flow chart of a method performed by the ICD of FIG. 1 that involves using virtual vector signals for detecting a shockable rhythm based on a change in the cardiac electrical axis.

FIG. 7 is a flow chart 400 of a method performed by ICD 14 using virtual vector signals for detecting a shockable rhythm based on a change in the cardiac electrical axis. At block 402, physical vector signals are received by virtual signal generator 93 from sensing module 86 during a known supraventricular rhythm. In some cases, the physical signals may be determined during different types of known supraventricular rhythms, for example supraventricular rhythms during normal sinus rhythm, during sinus tachycardia, or during conduction defects such as bundle branch block that may arise during sinus rhythm.

A desired number of virtual vector signal features are computed at block 404 from at least two physical vector signals at block 404. The virtual vector signal features may be determined by computing the virtual vector signals at predefined angles from the physical vector signals using trigonometric relations as described above. At block 406, cardiac signal analyzer determines the cardiac electrical axis for the known rhythm from among the physical and virtual vectors based on the determined virtual vector signal features. In one example, the cardiac electrical axis is the vector having the greatest absolute maximum peak R-wave amplitude or largest QRS signal among all of the available physical vector signals and computed virtual vector signals. In other examples, the cardiac electrical axis is identified as the physical or virtual vector having a signal with the highest ratio of the positive peak amplitude to negative peak amplitude from among all of the available physical vector signals and computed virtual vector signals.

In another example, the cardiac electrical axis is determined by identifying an isoelectric vector signal having a QRS signal that is substantially equally positive and negative. The isoelectric vector signal may be identified as a vector signal having a closest match between the negative area of the QRS signal and the positive area of the QRS signal or the closest match between the summed absolute values of negative QRS sample point amplitudes and the summed values of the positive QRS sample point amplitudes. The cardiac electrical axis is identified as one of the vectors that are 90 degrees from the isoelectric axis. The two opposing vectors that are +90 degrees and −90 degrees from the isoelectric vector may be compared. The vector having a substantially positive QRS signal is identified from the two opposing vectors as being the cardiac electrical axis.

The cardiac electrical axis may be determined during multiple known supraventricular rhythms, e.g., when the patient is known to have intermittent bundle branch block or non-sustained, non-conducted atrial tachyarrhythmia. After identifying and storing the cardiac electrical axis during the known supraventricular rhythm, cardiac signal monitoring for detecting a shockable rhythm begins at block 408 by selecting one or more of the physical and/or virtual vector signals for monitoring. Examples of methods for vector selection for cardiac signal monitoring at block 408 is described in greater detail below in conjunction with FIG. 8.

Tachyarrhythmia detector 94 analyzes the monitored cardiac signal(s) for detecting a suspected shockable rhythm according to an implemented detection algorithm. For example, a suspected shockable rhythm may be detected initially based on RR intervals and/or signal morphology criteria applied to the monitored cardiac signal(s). If a suspected shockable rhythm is detected at block 412, the tachyarrhythmia detector 94 determines if the cardiac electrical axis has changed compared to the cardiac electrical axis determined for the known supraventricular rhythm at block 414.

The virtual signal generator 93 computes the virtual vector signal features that were computed at block 404 and used to identify the cardiac electrical axis at block 406. The vector corresponding to the cardiac electrical axis is re-determined at block 414 as one of the available virtual and physical vectors. The same technique and criteria used for identifying the cardiac electrical axis during the known rhythm at block 406 may be used to identify the cardiac electrical axis during the unknown rhythm, e.g., the vector having a maximum QRS amplitude or the vector having a positive QRS signal that is orthogonal to a vector having an isoelectric vector signal feature.

In an alternative example, a virtual vector signal for the virtual vector identified as the cardiac electrical axis during the known supraventricular rhythm is computed at block 414. Features from the virtual vector signal are determined during the unknown rhythm and compared to features previously stored for the virtual vector cardiac electrical axis during the known supraventricular rhythm. If the features do not match, the cardiac electrical axis is determined to have changed during the unknown rhythm without having to compute all virtual vector signals and identifying the cardiac electrical axis during the unknown rhythm.

If the cardiac electrical axis during the unknown rhythm is not different than any of the cardiac electrical axes determined for known supraventricular rhythms, as determined at block 414, the suspected shockable rhythm is not confirmed. The unknown rhythm may be determined as a supraventricular, non-shockable rhythm at block 420. In response to not confirming the suspected shockable rhythm, a shock therapy is withheld at block 422. The process may loop back to block 410 to continue monitoring the selected vector signal(s) at block 410. In some cases, the cardiac electrical axis may have changed from a most recently determined cardiac electrical axis during a non-shockable rhythm to a cardiac electrical axis determined for a different non-shockable rhythm. In this case, a change in the non-shockable rhythm may be detected. For example, a spontaneous episode of bundle branch block or other non-shockable supraventricular rhythm may be detected at block 420.

If the virtual or physical vector identified as the cardiac electrical axis during the unknown rhythm is not the same virtual or physical vector identified as the cardiac electrical axis during the known supraventricular rhythm(s), as determined at block 414, a shockable rhythm may be detected at block 416. It is recognized that in some examples, additional shockable rhythm detection criteria may be required to be met in addition to a change in the cardiac electrical axis before detecting a shockable rhythm at block 416. In response to at least the change in cardiac electrical signal axis, a shock therapy may be delivered at block 424, or at least enabled and delivered pending other shockable rhythm detection criteria being met.

In some instances, it is assumed that the cardiac electrical axis will not change substantially between different non-shockable rhythms, such as normal sinus rhythm, sinus tachycardia, atrial tachycardia or atrial fibrillation or other supraventricular rhythms. Accordingly, it may be assumed that the physical or virtual vector identified as the cardiac electrical axis during a known supraventricular rhythm at block 406 will not change as long as the rhythm is a non-shockable rhythm. The cardiac axis may differ between different shockable rhythms depending on the electrical origin of the rhythm and the depolarization pathway. In some examples, the vector identified as the cardiac electrical axis may be stored at block 416 in response to detecting the shockable rhythm, along with other shockable rhythm data such as a sample cardiac electrical signal episode or cardiac signal features such as RR intervals or morphology features used to detect the shockable rhythm.

As cardiac electrical axis data are determined and stored for different shockable rhythms, shockable rhythms may be discriminated between each other based on the accumulated cardiac electrical axis data at block 418. For example, a patient may experience two or more different types of VT, such as one or more focal VT rhythms and one or more re-entrant VT rhythms that have different cardiac electrical axes and may or may not be characterized by different rates. Categorizing different VT rhythms based on an identified cardiac electrical axis may provide useful diagnostic information for making therapy delivery decisions.

For example, the success or failure of a therapy that is delivered at block 424 may be stored with the cardiac signal axis for the detected rhythm. In some cases, therapy control parameters such as therapy delivery vectors, shock energy, or other types of therapies, such as an anti-tachyarrhythmia therapy may be attempted before a therapy is successful in terminating the shockable rhythm. Once a therapy that is successful in terminating the shockable rhythm is identified, that therapy may be stored in conjunction with the cardiac electrical axis so that the same therapy may be used the next time a shockable rhythm is detected having the same cardiac electrical axis.

Figure 8:
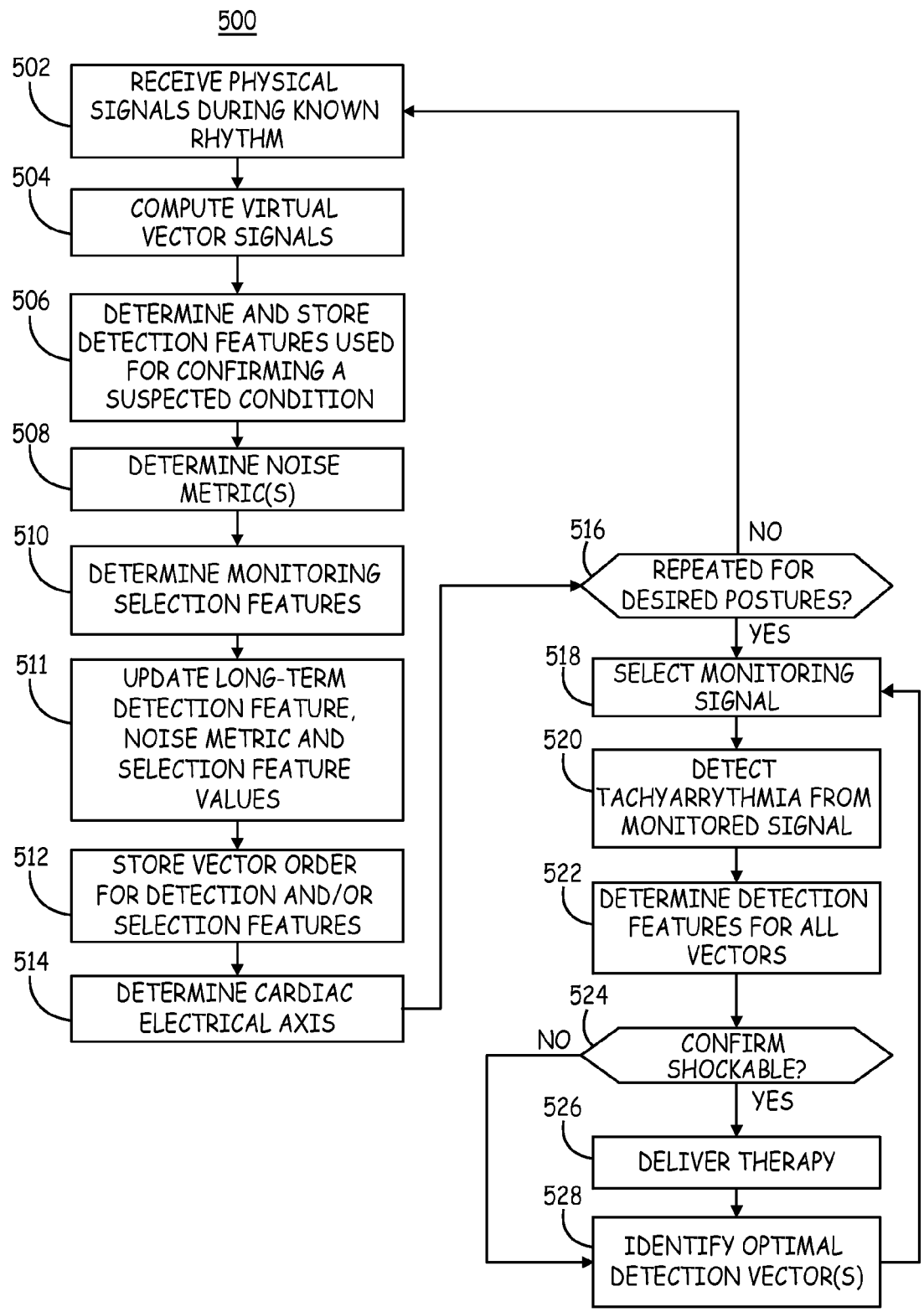
FIG. 8 is a flow chart of a method that may be performed by the IMD system of FIG. 1 for producing vector signal data used in selecting vector signals used during a monitoring and detection algorithm for detecting and confirming a suspected condition.

FIG. 8 is a flow chart 500 of a method that may be performed by IMD system 10 for selecting monitoring vector signals used to detect a suspected condition, selecting detection vector signals used by a detection algorithm for confirming a suspected condition and/or for establishing detection criteria. Operations included in FIG. 8 may be performed at the time of ICD implantation for selecting or recommending optimal virtual vector signals for use as monitoring or detection vector signals. The optimal virtual vector(s) for monitoring for a suspected condition and/or for confirming a suspected condition may be updated using the process shown in FIG. 8 (or a portion thereof) if a patient condition changes acutely (such as posture or activity) or chronically such as a myocardial infarction, patient weight gain or loss, ventricular hypertrophy, bundle branch block or other conduction defects, hyperkalemia, or other changes that may alter the physical vector signals and therefore alter the computed virtual vector signals or virtual vector signal features. Updates may be performed automatically by repeating the process shown in FIG. 8 or manually initiated by a user interacting with external device 40.

At block 502, at least two of the available physical sensing vector signals are received by the sensing module 86 during a known supraventricular rhythm. A desired number of virtual vector signals are computed from the physical vector signals at block 504 at predetermined angles from a physical sensing vector.

At blocks 506, 508 and 510, various signal features may be determined from each of the physical vector signals and each of the virtual vector signals for use in selecting at least one monitoring signal, at least one detection signal, which may be the same or different than the monitoring signal, and/or for establishing shockable rhythm detection criteria. At block 506, signal features are determined from the physical and virtual vector signals that are shockable rhythm detection features. These features are features that are determined during a suspected shockable rhythm and compared to shockable rhythm detection criteria for confirming a shockable rhythm. Such features may include normalized waveform area difference (NWAD), low slope content (LSC), normalized mean rectified amplitude, signal overall variability, or signal width, e.g., as generally disclosed in U.S. Pat. No. 8,301,233 (Zhang) or in U.S. Pat. No. 8,825, 145 (Zhang), both incorporated herein by reference in its entirety.

At block 508, noise metrics may be determined for each of the physical and virtual vector signals. Noise metrics may include a determination of a desired signal to noise ratio, such as a ratio of R-wave amplitude to T-wave amplitude or a determination of the presence of electromagnetic interference or non-cardiac myopotentials, e.g., based on a measurement of baseline signal variation. Noise metrics that may be determined may correspond to gross morphology parameters used to detect noise as disclosed in U.S. Pat. No. 8,437,842 (Zhang) and U.S. Pat. No. 7,496,409 (Greenhut, et al.), both incorporated herein.

At block 510, monitoring selection features may be determined. One or more virtual and/or physical vector signals may be monitored for detecting a suspected condition and one or more virtual or physical vector signals may be used for confirming a suspected condition. The virtual or physical vector signals used to monitor for a suspected condition may be referred to as the monitoring signal(s) and may be different signals than vector signals used to confirm the suspected condition in some examples. The virtual or physical vectors used to confirm a suspected may be referred to as the detection signal(s). Different signal features may be determined from the monitoring signal(s) for detecting a suspected condition than the features that are determined from the detection signals for confirming the suspected condition. As such, different selection features and criteria may be applied to the physical and virtual vector signals for selecting which vector signals are used as the monitoring signal(s) and which vector signals are used as the detection signal(s). In some examples, however, the features determined at blocks 504, 506 and 508 are not mutually exclusive since some features may be used for selecting both the monitoring signal(s) and the detection signal(s).

It is recognized that in some examples, the monitoring signals may be default physical vector signals and the detection signals are selected from the available physical and virtual vector signals so that computing virtual vector signals is performed when a suspected condition is already detected based on physical vector signals. In other examples, two out of the available physical and virtual vector signals may be selected as the monitoring signals based on noise metrics determined at block 508 and monitoring selection features determined at block 510. In one example, RR intervals are determined from the two monitoring signals for detecting a suspected shockable rhythm or suspected TWOS based on fast rate detection criteria. In this case, the monitoring selection features used to select the monitoring signals may include largest peak rectified R-wave amplitude, highest R-wave-to-T-wave amplitude ratio, highest difference between R-wave amplitude and T-wave amplitude, and lowest P-wave amplitude to promote reliable R-wave sensing and RR interval determinations. Some techniques for selecting a monitoring or detection signal may include methods generally disclosed in U.S. Pat. No. 7,496,409 (Greenhut, et al.), incorporated herein by reference in its entirety.

As described above, a vector signal having a minimum T-wave window signal energy may be identified for use in confirming suspected TWOS. Accordingly, the feature stored at block 506 for selecting a detection signal used to confirm TWOS is the feature of minimum T-wave window signal energy. A vector signal having the highest normalized waveform area of the QRS signal or lowest variability in normalized waveform area of the QRS signal may be selected for use as the detection vector for confirming a suspected shockable rhythm. A shockable rhythm may be confirmed when a normalized waveform area difference (NWAD) meets a shockable rhythm detection threshold. Methods for determining normalized QRS waveform area and NWAD for detecting a shockable rhythm are generally disclosed in the above-incorporated U.S. Pat. No. 8,825,145.

Since the features used to initially detect a suspected condition and the features used to confirm the suspected condition may be different, different features may be determined at blocks 506 for use in selecting a detection signal than at block 510 for use selecting a monitoring signal. Furthermore, since more than one type of suspected condition, such as TWOS and shockable rhythms, may need confirming, different detection vector(s) may be selected based on different signal feature criteria for confirming different suspected conditions. The features determined at block 506 may include features needed for selecting different detection vector signals for confirming different suspected conditions. Noise metrics may be used in addition to the signal features used for selecting a detection signal and in addition to the features used for selecting a monitoring signal.

Various features that may be determined for all available vectors at one of blocks 506, 508 and 510 may include, without limitation: rectified QRS signal amplitude, peak-to-peak QRS signal amplitude, R-wave amplitude to T-wave amplitude ratio, an R-wave polarity metric, summation of non-rectified QRS signal sample points or other metric of QRS signal phase, a T-wave polarity metric, low slope content, normalized waveform area, beat-to-beat template correlation, and baseline signal variation.

A polarity metric of the R-wave or the T-wave may be determined as the summation of non-rectified R-wave or T-wave signal sample points, respectively. Alternatively, a polarity metric of the R-wave or the T-wave may be determined as the ratio of, or difference between, the positive peak amplitude to baseline difference and the negative peak amplitude to baseline difference of the respective R-wave or T-wave. A ratio of 1 between the difference between the positive peak amplitude and the baseline and the difference between the negative peak amplitude and the baseline indicates a true biphasic signal. A ratio that is greater than one indicates a positive polarity, and a ratio that is less than one indicates a negative polarity. A polarity metric may alternatively be determined as a ratio of the maximum positive peak to the maximum negative peak.

The polarity metric(s) may be used in various examples for selecting a monitoring or detection signal or for establishing shockable rhythm detection criteria. For example, a physical or virtual vector signal having a polarity metric indicating the most monophasic QRS complex, e.g., based on a highest positive polarity metric of the R-wave, may be selected as a monitoring or detection signal. A physical or virtual vector signal having a polarity metric indicating the most biphasic T-wave of the virtual and physical signals may be identified as a detection signal having the lowest T-wave signal energy for use in confirming suspected T-wave oversensing. Conversely, a signal that is 90 degrees from the signal having the highest positive T-wave polarity metric may be selected as a monitoring or detection signal for use in confirming suspected T-wave oversensing.

In some examples, at least some of the detection features determined at block 506, the noise metrics determined at block 508, and/or the selection features determines at block 510 are used to update a long-term value of the respective detection feature, noise metric or selection feature. A long term value may be a running average of the feature or metric value determined during the current known rhythm and at least one previously determined value for the same feature or metric during a previous known supraventricular rhythm. A long term value may be determined over days, weeks, or months, for example, by averaging feature or metric values determined hourly, daily, or weekly. As described below, a monitoring or detection signal may be selected or recommended based on long term values of the detection features, noise metrics, and/or selection features alone or in combination with the currently determined detection features, noise metrics and/or selection features. Additionally or alternatively, shockable rhythm criteria may include a criterion based on the change in a signal feature during an unknown rhythm compared to the long-term value of the signal feature determined over multiple previous episodes of a known supraventricular rhythm.

At block 512, the physical and virtual vectors may be ordered according feature values determined at blocks 506, 508 and/or 510 and/or the long term feature or metric values determined at block 511 for each respective vector signal. The vector order may be stored from greatest to smallest feature value for each analogous one of one or more determined signal features. In some examples, criteria for confirming a suspected condition include a change in the vector order for a given signal feature, e.g., a change in the vector order of maximum peak R-wave amplitude, R-wave polarity metric, or T-wave polarity metric.

In addition to or alternatively to storing at least one vector order based on signal feature values or noise metrics, the cardiac electrical axis is determined at block 514 using the techniques disclosed in conjunction with FIG. 7. In other examples, the vector having a signal resulting in the highest positive polarity of the R-wave based on a polarity metric may be identified at block 514 as the cardiac electrical axis during the known rhythm.

In some examples, the patient may experience bundle branch block or other conduction defects that may be intermittent and cause changes in the physical vector signals, and therefore cause changes in the computed virtual vector signals, even when a shockable rhythm is not occurring. In order to account for changes in signal features or the cardiac electrical axis due to conduction defects during a non-shockable rhythm, the detection features, noise metrics, selection features, long term values, vector orders, and/or cardiac electrical axis determined at blocks 506 through 514 may be labeled according to the known cardiac rhythm which may include identifying a conduction defect, such as bundle branch block, present during the known cardiac rhythm. A signal feature, cardiac electrical axis or vector order during an unknown rhythm may then be compared to the analogous signal feature, vector order or cardiac electrical axis determined during the known rhythm with a conduction defect and during the known rhythm without the conduction defect to avoid falsely detecting a shockable rhythm due to the influence of a conduction defect on the detection signals.

Once various signal features, feature-dependent vector order, and/or cardiac electrical axis are stored at blocks 506, 508, 510, 512 and 514 for the known supraventricular rhythm during a first patient body posture, the process of blocks 502 through 514 may be repeated for different patient postures as indicated at block 516. A given vector signal may change due to a change in patient body position. In some examples, signal features, feature-dependent vector order, and/or cardiac electrical axis are determined for multiple patient body postures so that cardiac signal analyzer 90 can select monitoring and/or detection signals that are optimal for a given posture and/or select the appropriate feature values, vector order, and/or cardiac axis determined during a known rhythm and body posture for comparison for confirming a suspected condition during an unknown rhythm and the same body posture.

Patient posture may be established during the steps performed at blocks 502 through 514 under the direction of a clinician or a posture sensor may be included in sensors 96 for detecting a posture signal. Signal features, one or more feature-dependent vector orders, and/or the cardiac electrical axis may be labeled in memory 82 based on a detected posture signal at the time that the values are stored. A multi-axis accelerometer that may be used for detecting patient posture is generally disclosed in U.S. Pat. No. 5,593,431 (Sheldon), hereby incorporated herein by reference in its entirety.

At block 518, a monitoring signal is selected based on the features determined at blocks 510 and 512. The monitoring signal may be selected based on determining a posture sensor signal, comparing the signal features stored for the current posture for each of the physical and virtual vector signals, and selecting a monitoring signal based on monitoring signal selection criteria. For example, a monitoring signal may be selected based on a lowest baseline noise metric, a highest R-wave amplitude to T-wave amplitude ratio, lowest P-wave amplitude and highest R-wave amplitude or any combination thereof. In some examples, the monitoring signal is selected based on a long term value of a monitoring selection feature or a weighted combination of the most recently determined monitoring selection feature during a known rhythm and the long term value of the monitoring selection feature during multiple episodes of the known rhythm.

In one example, the vector having the overall highest ranking when vectors are ordered according these features is selected as the monitoring signal. A vector order may be stored from lowest to highest baseline noise metric, highest to lowest R-wave amplitude to T-wave amplitude ratio, lowest to highest P-wave amplitude and highest to lowest R-wave amplitude. An overall vector ranking may be determined based on the individual vector order ranking for each of these four features. For example, the overall vector order ranking may be a sum, weighted sum, average, or median of the individual vector order rankings. The vector having the highest overall vector ranking (i.e., lowest sum) is selected as the monitoring vector.

Once the monitoring signal is selected, the signal is monitored for detecting a tachyarrhythmia at block 520, e.g. based on detecting a fast heart rate as described previously. At block 522, detection features that were stored at block 506 are determined for all physical and virtual vectors during the tachyarrhythmia. The tachyarrhythmia is confirmed as being a shockable rhythm at block 524. Confirmation at block 524 may be based on a change in cardiac electrical axis, a change in vector order for a given feature or other shockable rhythm criteria. In some examples, the tachyarrhythmia detected at block 520 may be induced VT or VF, e.g., following delivery of a tachyarrhythmia induction shock during ICD testing.

If a shockable rhythm is confirmed at block 524, therapy is delivered at block 526 to terminate the shockable rhythm. At block 528, a comparative analysis of the vector signal features determined at block 522 is performed, which may include ordering vectors according to a value of a detection feature, to identify an optimal detection vector. A feature used to confirm a suspected shockable rhythm may be determined from each physical and virtual vector signal at block 522 and compared to the analogous feature determined for the respective vector at block 506 during the known supraventricular rhythm. The vector, physical or virtual, having the greatest separation or difference between the detection feature determined during the known supraventricular rhythm and the analogous detection feature determined during the confirmed shockable rhythm or its long term value may be identified as the optimal detection vector.

In some examples, if the shockable rhythm is not confirmed, the comparative analysis performed at block 528 may identify vector(s) having the least change in a detection feature during the unconfirmed shockable rhythm compared to during the detection feature during the known supraventricular rhythm. As such, a detection vector may be identified, for a given patient body posture, that has a relatively low variation of a detection feature during non-shockable rhythms and a relatively high change in the detection feature due to a shockable rhythm.

In some instances, ICD 14 performs the operations shown in FIG. 8. In other examples, ECG signal data may be transmitted to external device 40 and external device processor 52 may perform some of the operations performed in FIG. 8 for identifying optimal monitoring and detection vectors. In some examples, selecting an optimal monitoring vector and/or optimal detection vector includes automatically programming the vector for use by the cardiac signal analyzer 90 for detecting and confirming a suspected condition. In other examples, selecting an optimal monitoring vector and/or detection vector includes displaying the selected vector on the display of the external device 40 as a recommended vector to allow a user to accept the selected vector(s) and enable programming of the selected vector(s).

Figure 9:
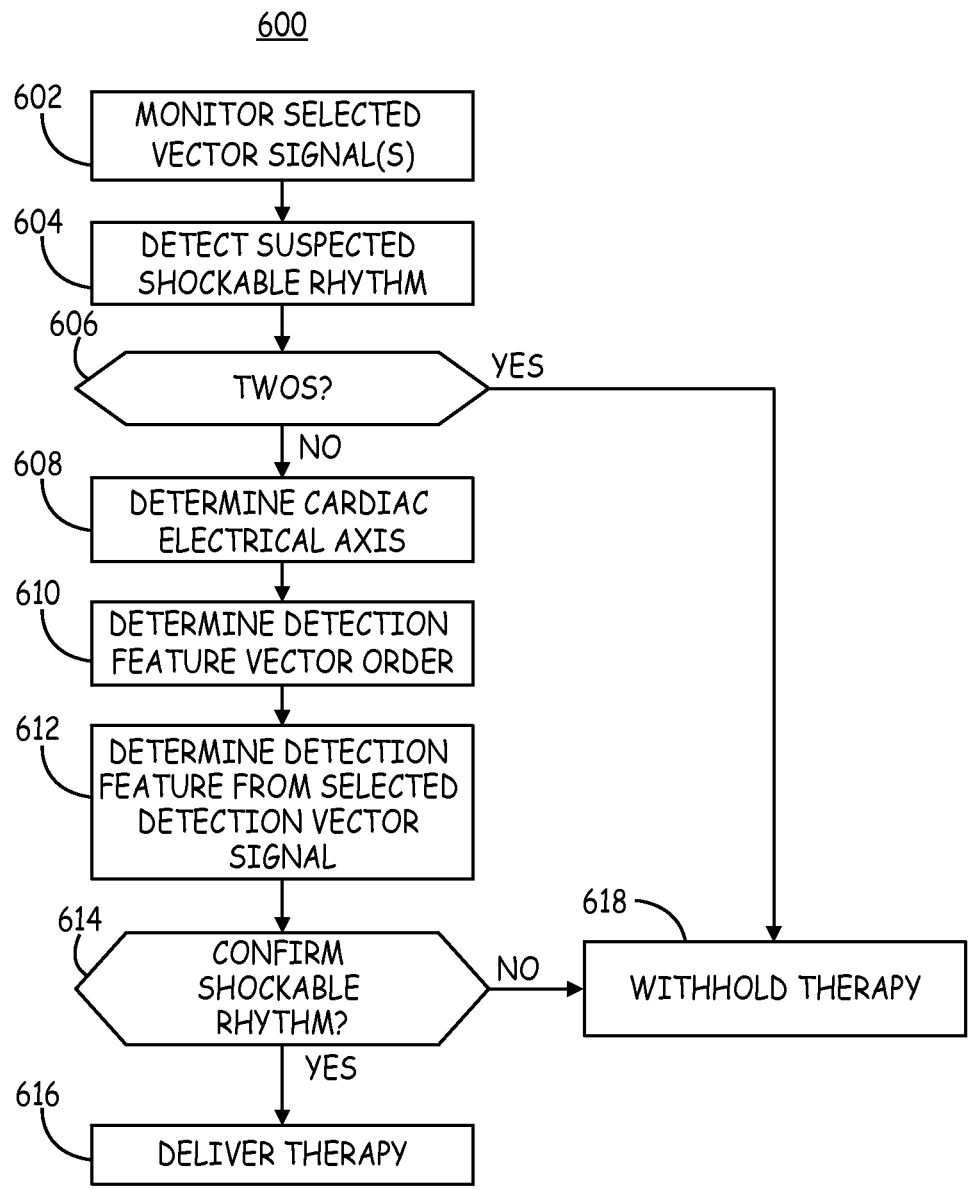
FIG. 9 is a flow chart of a method for detecting and confirming a shockable rhythm according to one example.

FIG. 9 is a flow chart 600 of a method for detecting and confirming a shockable rhythm by ICD 14 according to one example. Cardiac rhythm monitoring is performed according to the process shown in flow chart 600 after obtaining data from the physical and virtual vector signals according to the flow chart 500 of FIG. 8 for selecting at least one optimal monitoring vector for detecting a suspected condition, selecting at least one optimal detection vector for confirming the suspected condition and/or establishing a signal feature vector order and/or cardiac electrical axis during a non-shockable rhythm for confirming the suspected condition.

At block 602, at least one vector signal may be selected as a monitoring signal from the physical and virtual vector signals as described above based on a signal selection feature, a noise metric, patient body posture, or any combination thereof. In other examples, the vector signal(s) for monitoring for a suspected condition include only physical vector signals. At block 604, a suspected shockable rhythm is detected from the selected monitoring signal(s), e.g. based on detecting RR intervals meeting shockable rhythm criteria. One example of RR interval shockable rhythm criteria includes at least 12 out of 18 consecutive RR intervals being less than 300 ms.

In some examples, at block 606, the cardiac signal analyzer 90 may determine if TWOS is causing the fast rhythm detection made at block 604. TWOS may be confirmed by determining the T-wave window signal energy of a vector signal previously identified as having minimum T-wave window signal energy as described above in conjunction with FIG. 6A. TWOS may alternatively be confirmed based on a difference between the T-wave window signal energy of consecutive pairs of T-wave windows of at least one virtual vector as described in conjunction with FIG. 6B. If TWOS is confirmed based on detecting no increase in the T-wave window signal energy at block 606, shockable rhythm therapy is withheld at block 618. The suspected shockable rhythm detected at block 604 is not confirmed.

If TWOS is not confirmed at block 606, the cardiac electrical axis may be determined at block 608 as described in conjunction with FIG. 7 above. Additionally or alternatively, a shockable rhythm detection feature vector order is determined at block 610 and/or a detection feature is determined from a selected detection vector at block 612. The detection vector may be selected at block 612 based on the detection features determined at block 506 of FIG. 8 and optionally based on noise metrics determined at block 508, selection features determined at block 510, and/or patient posture.

At block 614, the cardiac electrical axis determined at block 608 during the suspected shockable rhythm is compared to the cardiac electrical axis previously determined during a known supraventricular rhythm. Additionally or alternatively, the vector order determined at block 610 based on values of an analogous detection feature of each physical and virtual vector signal during the current unknown rhythm is compared to the vector order stored for the detection feature during the known supraventricular rhythm. The detection feature from the detection vector signal, if determined at block 612, may be compared to shockable rhythm detection criteria, which may include determining a change in the detection feature during the suspected shockable rhythm from the value of the detection feature determined from the same vector, virtual or physical, during the known supraventricular rhythm.

A shockable rhythm may be confirmed at block 614 in response to detecting a change in the cardiac electrical axis, a change in the detection feature vector order, a change in the detection feature determined at block 612 meeting a shockable rhythm detection feature, or any combination thereof. If a shockable rhythm is confirmed, the therapy delivery module 84 is controlled by control module 80 to deliver a therapy at block 616. If the rhythm is not confirmed as a shockable rhythm at block 614, therapy is withheld at block 618.

Thus, a method and apparatus for using virtual vector cardiac electrical signals for detecting and confirming suspected conditions have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A method performed by a medical device, comprising:
    receiving at least two physical cardiac electrical signals from a patient's heart via a plurality of electrodes that define at least two physical sensing vectors;
    computing a plurality of virtual cardiac electrical signals using the at least two physical cardiac electrical signals during a first, known cardiac rhythm, each of the plurality of virtual cardiac electrical signals corresponding to one of a plurality of virtual sensing vectors extending at a respective one of a plurality of angles relative to one of the at least two physical sensing vectors, wherein computing the plurality of virtual cardiac electrical signals comprises calculating a projection of the at least two physical cardiac electrical signals along each of the plurality of virtual sensing vectors;
    determining, for each of the plurality of virtual cardiac electrical signals, a plurality virtual cardiac electrical signal features;
    comparing the determined signal features;
    establishing criteria for confirming a suspected condition in response to the comparing;
    detecting a suspected condition during a second, unknown cardiac rhythm; and
    confirming the suspected condition in response to the established criteria being met during the second, unknown cardiac rhythm.

2. The method of claim 1, wherein:
    establishing the criteria for confirming the suspected condition comprises determining one of the at least two physical sensing vectors and the plurality of virtual sensing vectors as a cardiac electrical axis based on the comparing during the first, known cardiac rhythm;
    confirming the suspected condition comprises determining a different one of the at least two physical sensing vectors and the plurality of virtual sensing vectors as the cardiac electrical axis during the second, unknown cardiac rhythm.

3. The method of claim 2, wherein determining one of the at least two physical sensing vectors and the plurality of virtual sensing vectors as the cardiac electrical axis comprises:
    identifying an isoelectric cardiac electrical signal feature from among the at least two physical sensing vectors and the plurality of virtual sensing vectors;
    identifying a vector of the isoelectric cardiac electrical signal feature; and
    selecting a vector orthogonal to the identified vector of the isoelectric cardiac electrical signal feature as the cardiac electrical axis.

4. The method of claim 2, wherein determining one of the at least two physical sensing vectors and the plurality of virtual sensing vectors as the cardiac electrical axis comprises:
  determining a maximum peak R-wave amplitude for each of the at least two physical sensing vectors and the plurality of virtual sensing vectors;
  comparing the determined maximum peak R-wave amplitudes to identify a greatest maximum peak R-wave amplitude; and
  identifying the cardiac electrical axis as one of the at least two physical sensing vectors and the plurality of virtual sensing vectors having the greatest maximum peak R-wave amplitude.

5. The method of claim 1,
  wherein establishing the criteria for confirming the suspected condition comprises determining a first order of at least the plurality of virtual sensing vectors based on the comparing of the signal features determined during the first, known cardiac rhythm; the method further comprising determining a second order of at least the plurality of virtual sensing vectors based on determining and comparing the signal features for the plurality of virtual cardiac electrical signals during the second, unknown cardiac rhythm; and
  wherein confirming the suspected condition comprises confirming the suspected condition in response to the first order being different than the second order.

6. The method of claim 5, wherein determining the first order and the second order comprises ranking the determined signal features from largest to smallest.

7. The method of claim 1,
  wherein establishing the criteria for confirming the suspected condition comprises identifying one of the at least two physical sensing vectors and the plurality of virtual sensing vectors having a lowest T-wave window signal energy; and
  wherein confirming the suspected condition comprises:
    redetermining the T-wave window signal energy during the second, unknown rhythm from the identified vector having the lowest T-wave window signal energy during the first, known cardiac rhythm; and
    detecting an increase in the T-wave window signal energy of the identified vector.

8. The method of claim 7, further comprising detecting T-wave oversensing in response to the T-wave window signal energy during the second, unknown rhythm not being greater than the T-wave window signal energy during the first, known cardiac rhythm.

9. The method of claim 1, wherein establishing the criteria for confirming the suspected cardiac condition comprises:
  determining the signal features for each of the at least two physical sensing vectors and the plurality of virtual sensing vectors during a third cardiac rhythm,
  identifying one of the at least two physical sensing vectors and the plurality of virtual sensing vectors having a greatest difference between the signal feature determined during the first, known cardiac rhythm and the signal feature determined during the third cardiac rhythm, the first known cardiac rhythm being a non-shockable rhythm and the third cardiac rhythm being a shockable rhythm.

10. The method of claim 1, further comprising:
  selecting a detection vector among the at least two physical sensing vectors and the plurality of virtual sensing vectors based on the comparing;
  wherein confirming the suspected condition in response to the established criteria comprises determining a cardiac electrical signal feature of the detection vector during the second, unknown cardiac rhythm.

11. The method of claim 10, further comprising:
  selecting a monitoring vector from among the at least two physical sensing vectors and the plurality of virtual sensing vectors;
  wherein detecting the suspected condition comprises detecting the suspected condition in response to a signal feature of the monitoring vector.

12. The method of claim 10, wherein selecting the detection vector comprises identifying among the at least two physical sensing vectors and the plurality of virtual sensing vectors a vector having at least one of: a lowest T-wave amplitude, a highest R-wave amplitude, a highest R-wave amplitude to T-wave amplitude ratio, a highest R-amplitude and T-wave amplitude difference, a most biphasic T-wave signal, a most monophasic R-wave signal, a lowest baseline noise metric, a highest low slope content, a highest normalized waveform area, and a lowest waveform variability metric.

13. The method of claim 1, further comprising:
  detecting a plurality of different patient body posture signals during the first, known rhythm;
  repeating the steps of receiving, computing, determining, comparing and establishing for each of the plurality of the patient body posture signals;
  wherein confirming the suspected condition in response to the established criteria being met during the second, unknown cardiac rhythm comprises detecting a body posture signal during the second, unknown cardiac rhythm and using the criteria established during a matching one of the plurality of different patient body posture signals during the first, known cardiac rhythm.

14. The method of claim 1, wherein confirming the suspected condition comprises detecting a shockable rhythm, the method further comprising delivering a therapy to the patient's heart in response to detecting the shockable rhythm.

15. The method of claim 1, further comprising:
  detecting a plurality of cardiac events comprising suspected T-wave oversensed events in response at least one of the physical cardiac electrical signals;
  for at least two of the plurality of cardiac events comprising suspected T-wave oversensed events, set a T-wave window of at least one of the virtual sensing vectors;
  determine a first T-wave window signal energy and a second T-wave window signal energy of the at least one virtual sensing vector; and
  confirm T-wave oversensing based on a difference between the first T-wave window signal energy and the second T-wave window signal energy.

16. The method of claim 1, further comprising:
  determining the plurality of virtual cardiac electrical signal features during a third, known cardiac rhythm;
  determine a long term value of each of the plurality of virtual cardiac electrical signal features using the plurality of virtual cardiac electrical signal features determined during the third, known cardiac rhythm and the plurality of virtual cardiac electrical signal features determined during the first, known cardiac rhythm;
  comparing the long term values; and
  selecting a vector from among the virtual sensing vectors based on comparing the long term values for use in at least one of detecting the suspected condition and confirming the suspected condition.

17. The method of claim 1, further comprising:
identifying one of the at least two physical sensing vectors and the plurality of virtual sensing vectors as a first cardiac electrical axis during the first, known cardiac rhythm based on the plurality of virtual cardiac electrical signal features determined during the first, known cardiac rhythm;
determining a plurality of virtual cardiac electrical signal features during the second, unknown cardiac rhythm;
identifying one of the at least two physical sensing vectors and the plurality of virtual sensing vectors as a second cardiac electrical axis during the second, unknown cardiac rhythm based on the plurality of virtual cardiac electrical signal features determined during the second, unknown cardiac rhythm;
determining a plurality of virtual cardiac electrical signal features during a third, known cardiac rhythm;
identifying one of the at least two physical sensing vectors and the plurality of virtual sensing vectors as a third cardiac electrical axis during the third, known cardiac rhythm based on the plurality of virtual cardiac electrical signal features determined during the third known, cardiac rhythm; and
detecting the second unknown cardiac rhythm as one of the first known cardiac rhythm and the third known cardiac rhythm in response to the second cardiac electrical axis identified during the second, unknown cardiac rhythm matching a respective one of the first cardiac electrical axis and the third cardiac electrical axis.

18. A medical device system, comprising:
a sensing module configured to receive at least two physical cardiac electrical signals via a plurality of electrodes that define at least two physical sensing vectors; and
a control module coupled to the sensing module and configured to:
compute a plurality of virtual cardiac electrical signals using the at least two physical cardiac electrical signals during a first, known cardiac rhythm, each of the plurality of virtual cardiac electrical signals corresponding to one of a plurality of virtual sensing vectors extending at a respective one of a plurality of angles relative to one of the at least two physical sensing vectors, wherein computing the plurality of virtual cardiac electrical signals comprises calculating a projection of the at least two physical cardiac electrical signals along each of the plurality of virtual sensing vectors;
determine, for each of the plurality of virtual cardiac electrical signals, a plurality of virtual cardiac electrical signal features;
comparing the determined signal features;
establishing criteria for confirming a suspected condition in response to the comparing;
detecting a suspected condition during a second, unknown cardiac rhythm; and
confirming the suspected condition in response to the established criteria being met during the second, unknown cardiac rhythm.

19. The system of claim 18, wherein the control module is configured to:
establish the criteria for confirming the suspected condition by determining one of the at least two physical sensing vectors and the plurality of virtual sensing vectors as a cardiac electrical axis based on the comparing during the first, known cardiac rhythm;
confirm the suspected condition by determining a different one of the at least two physical sensing vectors and the plurality of virtual sensing vectors as the cardiac electrical axis during the second, unknown cardiac rhythm.

20. The system of claim 19, wherein the control module is configured to determine one of the at least two physical sensing vectors and the plurality of virtual sensing vectors as the cardiac electrical axis by:
identifying an isoelectric cardiac electrical signal feature from among the at least two physical sensing vectors and the plurality of virtual sensing vectors;
identifying a vector of the isoelectric cardiac electrical signal feature; and
selecting a vector orthogonal to the identified vector of the isoelectric cardiac electrical signal feature as the cardiac electrical axis.

21. The system of claim 19, wherein the control module is configured to determine one of the at least two physical sensing vectors and the plurality of virtual sensing vectors as the cardiac electrical axis by:
determining a maximum peak R-wave amplitude for each of the at least two physical sensing vectors and the plurality of virtual sensing vectors;
comparing the determined maximum peak R-wave amplitudes to identify a greatest maximum peak R-wave amplitude; and
identifying the cardiac electrical axis as one of the at least two physical sensing vectors and the plurality of virtual sensing vectors having the greatest maximum peak R-wave amplitude.

22. The system of claim 18, wherein the control module is configured to:
establish the criteria for confirming the suspected condition by at least determining a first order of at least the plurality of virtual sensing vectors based on the comparing of the signal features determined during the first, known cardiac rhythm;
determine a second order of at least the plurality of virtual sensing vectors based on determining and comparing the signal features for the plurality of virtual cardiac electrical signals during the second, unknown cardiac rhythm; and
confirm the suspected condition in response to the first order being different than the second order.

23. The system of claim 22, wherein the control module is configured to determine the first order and the second order by ranking the determined signal features from largest to smallest.

24. The system of claim 18, wherein the control module is configured to:
establish the criteria for confirming the suspected condition by at least identifying one of the at least two physical sensing vectors and the plurality of virtual sensing vectors having a lowest T-wave window signal energy; and
confirm the suspected condition by:
redetermining the T-wave window signal energy during the second, unknown rhythm from the identified vector having the lowest T-wave window signal energy during the first, known cardiac rhythm; and
detecting an increase in the T-wave window signal energy of the identified vector.

25. The system of claim 24, wherein the control module is further configured to detect T-wave oversensing in response to the T-wave window signal energy not being greater during the second, unknown rhythm compared to the T-wave window signal energy during the first, known cardiac rhythm.

26. The system of claim 18, wherein the control module is further configured to establish the criteria for confirming the suspected cardiac condition by:
   determining the signal features for each of the at least two physical sensing vectors and the plurality of virtual sensing vectors during a third cardiac rhythm,
   identifying one of the at least two physical sensing vectors and the plurality of virtual sensing vectors having a greatest difference between the signal feature determined during the first, known cardiac rhythm and the signal feature determined during the third cardiac rhythm, the first known cardiac rhythm being a non-shockable rhythm and the third cardiac rhythm being a shockable rhythm.

27. The system of claim 18, wherein the control module is configured to:
   select a detection vector among the at least two physical sensing vectors and the plurality of virtual sensing vectors based on the comparing;
   wherein confirming the suspected condition in response to the established criteria comprises determining a cardiac electrical signal feature from the detection vector during the second, unknown cardiac rhythm.

28. The system of claim 27, wherein the control module is further configured to:
   select a monitoring vector from among the at least two physical sensing vectors and the plurality of virtual sensing vectors; and
   wherein detecting the suspected condition comprises detecting the suspected condition in response to a signal feature of the monitoring vector.

29. The system of claim 27, wherein the control module is configured to select the detection vector by identifying among the at least two physical vectors and the plurality of virtual sensing vectors at least one of: a lowest T-wave amplitude, a highest R-wave amplitude, a highest R-wave amplitude to T-wave amplitude ratio, a highest R-amplitude and T-wave amplitude difference, a most biphasic T-wave signal, a most monophasic R-wave signal, a lowest baseline noise metric, a highest low slope content, a highest normalized waveform area, and a lowest waveform variability metric.

30. The system of claim 18, further comprising a posture sensor, wherein the control module is further configured to:
   detect a plurality of different patient body posture signals during the first, known rhythm;
   repeat the steps of receiving, computing, determining, comparing and establishing for each of the plurality of the patient body posture signals; and
   confirm the suspected condition in response to the established criteria being met during the second, unknown cardiac rhythm by detecting a body posture signal during the second, unknown cardiac rhythm and using the criteria established during a matching one of the plurality of different patient body posture signals during the first, known cardiac rhythm.

31. The system of claim 18, further comprising a therapy delivery module configured to generate and deliver a therapy to the patient's heart via the plurality of electrodes;
   wherein the control module is configured to confirm the suspected condition by detecting a shockable rhythm and control the therapy delivery module to deliver the therapy in response to detecting the shockable rhythm.

32. The system of claim 18, wherein:
   the sensing module is configured to detect a plurality of cardiac events comprising suspected T-wave oversensed events in response at least one of the physical cardiac electrical signals;
   the control module is configured to:
      for at least two of the plurality of cardiac events comprising suspected T-wave oversensed events, set a T-wave window of at least one of the virtual sensing vectors;
      determine a first T-wave window signal energy and a second T-wave window signal energy of the at least one virtual sensing vector; and
      confirm T-wave oversensing based on a difference between the first T-wave window signal energy and the second T-wave window signal energy.

33. The system of claim 18, wherein the control module is further configured to:
   determine the plurality of virtual cardiac electrical signal features during a third, known cardiac rhythm;
   determine a long term value of each of the plurality of virtual cardiac electrical signal features using the plurality of virtual cardiac electrical signal features determined during the third, known cardiac rhythm and the plurality of virtual cardiac electrical signal features determined during the first, known cardiac rhythm;
   comparing the long term values; and
   selecting a vector from among the virtual sensing vectors based on comparing the long term values for use in at least one of detecting the suspected condition and confirming the suspected condition.

34. The system of claim 18, wherein the control module is further configured to:
   identify one of the at least two physical sensing vectors and the plurality of virtual sensing vectors as a first cardiac electrical axis during the first known cardiac rhythm based on the plurality of virtual cardiac electrical signal features determined during the first known cardiac rhythm;
   determine a plurality of virtual cardiac electrical signal features during the second unknown cardiac rhythm;
   identify one of the at least two physical sensing vectors and the plurality of virtual sensing vectors as a second cardiac electrical axis during the second unknown cardiac rhythm based on the plurality of virtual cardiac electrical signal features determined during the second, unknown cardiac rhythm;
   determine a plurality of virtual cardiac electrical signal features during a third known cardiac rhythm;
   identify one of the at least two physical sensing vectors and the plurality of virtual sensing vectors as a third cardiac electrical axis during the third, known cardiac rhythm based on the plurality of virtual cardiac electrical signal features determined during the third known cardiac rhythm; and
   detect the second unknown cardiac rhythm as one of the first known cardiac rhythm and the third known cardiac rhythm in response to the second cardiac electrical axis identified during the second unknown cardiac rhythm matching a respective one of the first cardiac electrical axis and the third cardiac electrical axis.

35. The system of claim 18, further comprising a medical electrical lead coupled to the sensing module and carrying at least a portion of the plurality of electrodes.

36. A non-transitory, computer-readable storage medium comprising a set of instructions which, when executed by a control module of a medical device, cause the medical device to:
  receive at least two physical cardiac electrical signals from a patient's heart via a plurality of electrodes that define at least two physical sensing vectors;
  compute a plurality of virtual cardiac electrical signals using the at least two physical cardiac electrical signals during a first, known cardiac rhythm, each of the plurality of virtual cardiac electrical signals corresponding to one of a plurality of virtual sensing vectors extending at a respective one of a plurality of angles relative to one of the at least two physical sensing vectors, wherein computing the plurality of virtual cardiac electrical signals comprises calculating a projection of the at least two physical cardiac electrical signals along each of the plurality of virtual sensing vectors;
  determine, for each of the plurality of virtual cardiac electrical signals, one or more virtual cardiac electrical signal features;
  compare the determined signal features;
  establish criteria for confirming a suspected condition in response to the comparing;
  detect a suspected condition during a second, unknown cardiac rhythm; and
  confirm the suspected condition in response to the established criteria being met during the second, unknown cardiac rhythm.

* * * * *